(12) United States Patent
Yoneda et al.

(10) Patent No.: US 6,214,859 B1
(45) Date of Patent: Apr. 10, 2001

(54) ETHYLAMINE DERIVATIVES

(75) Inventors: Fumio Yoneda, Osaka (JP); Joseph Knoll, Budapest (HU); Hironori Ode, Osaka (JP); Masatoshi Sakae, Osaka (JP); Masanori Katurada, Osaka (JP); Toshiaki Moto, Osaka (JP); Takashi Ando, Osaka (JP); Seiichiro Shimazu, Osaka (JP); Kazue Takahata, Osaka (JP); Michitaro Fujimoto, Osaka (JP)

(73) Assignee: Fujimoto Brothers Co., Ltd., Osaka (JP)

( * ) Notice: Subject to any disclaimer, the term of this patent is extended or adjusted under 35 U.S.C. 154(b) by 0 days.

(21) Appl. No.: 09/269,718

(22) PCT Filed: Aug. 3, 1998

(86) PCT No.: PCT/JP98/03468

§ 371 Date: Jul. 12, 1999

§ 102(e) Date: Jul. 12, 1999

(87) PCT Pub. No.: WO99/07667

PCT Pub. Date: Feb. 18, 1999

(30) Foreign Application Priority Data

Aug. 7, 1997 (JP) .................................................. 9-247445

(51) Int. Cl.$^7$ ...................... A61K 31/36; A61K 31/403; C07D 209/14; C07D 317/58; C07D 333/58

(52) U.S. Cl. .......................... 514/419; 514/443; 514/465; 548/484; 548/503; 549/49; 549/51; 549/441; 549/454; 564/454

(58) Field of Search .................................. 514/419, 443, 514/465, 470; 548/484, 503; 549/51, 49, 440, 441, 466, 467; 564/454

(56) References Cited

U.S. PATENT DOCUMENTS

| | | | |
|---|---|---|---|
| 3,296,072 | * | 1/1967 | Szmuszkovicz et al. . |
| 3,883,560 | | 5/1975 | Colgate et al. . |
| 5,494,928 | * | 2/1996 | Bos . |
| 5,627,200 | | 5/1997 | Pfizer et al. . |

FOREIGN PATENT DOCUMENTS

| | | |
|---|---|---|
| 1198128 | 7/1970 | (GB) . |
| 7-149723 | 6/1995 | (JP) . |
| 98-34646 | 8/1998 | (WO) . |

OTHER PUBLICATIONS

Chemical Abstract, vol. 125, 1996, Abstract No. 125:265667, Moreau, J.L. et al., "5HT2C Receptor Agonists Exhibit Antidepressant–like Properties in the Anhedonia Model of Depression in Rats", Eur. Neuropsychopharmacol., 1996, vol. 6, No. 3, pp. 169–175.

Simantov, Rabi, "Neurotransporters at the Jucture of Drug Action: Role in Programmed Cell Death, and Toxicity of Abused MDMA", Nato ASI Ser., Ser. H, 1997, vol. 100, pp. 237–248.

McGrath, C. et al., "Effect of Acute Administration of 3,4–methylenedioxymethamphetamine (MDMA) on Temperature and Locomotor Activity in the olfactory Bulbectomized Rate Model of Depression", Med. Sci. Res., 1995, vol. 23, No. 3, pp. 199–201.

White, S.R. et al., "Methylenedioxymethamphetamine Depresses Glutamate–evoked Neuronal Firing and Increases Extra–cellular Levels of Dopamine and Serotonin in the Nucleus Accumbens in vivo", Neuroscience, Oxford, 1994, vol. 62, No. 1, pp. 41–50.

Piercey, M.F. et al., "Effects of MDMA ("Extacy") on Firing Rates of Serotonergic, Dopaminergic, and Noradrenergic Neurons in the Rat", Brain Res., 1990, vol. 526, No. 2, pp. 203–206.

Ricaurte, G.A. et al., "3,4–Methylenedioxymethamphetamine, Serotonin and Memory", J. Pharmacol. Exp. Ther., 1993, vol. 226, No. 2, pp. 1097–1106.

Lehman, J. et al., "Regional Distribution to Recovery of 5–HT Levels after Administration of 'Atrophins' MDMA and D,L–Fenfluramine. Stereospecificity and Comparison with 5,7–Dihydroxytryptamine", Ann, N.Y. Acad. Sci., 1992, vol. 648, pp. 291–295.

(List continued on next page.)

*Primary Examiner*—Joseph K. McKane
(74) *Attorney, Agent, or Firm*—Wenderoth, Lind & Ponack, L.L.P.

(57) ABSTRACT

Ethylamine derivatives of the formula (I):

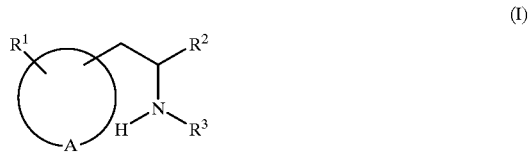

(wherein $R^1$ is hydrogen, hydroxyl, lower alkoxy or halogen; $R^2$ is alkyl having 2 to 5 carbon atoms; $R^3$ is hydrogen, alkyl having 2 to 5 carbon atoms, alkylcarbonyl having 2 to 5 carbon atoms, aryl having 6 to 10 carbon atoms or arylalkyl having 7 to 11 carbon atoms; the ring is a bicyclic compound which consists of at least one benzene ring and may comprise a saturated or unsaturated five- or six-membered ring which may or may not have heteroatoms, providing that when the ring is indole or 1,3-benzodioxole, $R^2$ and $R^3$ do not constitute, at the same time, two carbon atoms members, and when $R^3$ is hydrogen, the ring is a bicyclic compound which is not indole, benzothiophene or benzodioxole and $R^2$ is alkyl having 3 to 5 carbon atoms and pharmaceutically acceptable acid addition salts thereof. These compounds are promising as psychotropic drugs, antidepressants, drugs for Parkinson's disease and/or drugs for Alzeimer's disease.

11 Claims, 9 Drawing Sheets

OTHER PUBLICATIONS

Chemical Abstract, vol. 64, No. 12, 1966, Abstract No. 64:17522d, "Synthesis and Pharmacological Activity of Alkylated Tryptamines", J. Med. Chem., 1966, vol. 9, No. 3, pp. 341–344.

Chemical Abstract, vol. 64, No. 4, 1966, Abstract No. 64:5032f, "The Indole Series. I. Indolyl–alkylamines", J. Chem. Soc., 1965, pp. 7165–7178.

Chemical Abstract, vol. 63, No. 8, 1965, Abstract No. 63:9840e, "Synthesis of New Compounds in the Amphetamine Group, ", Acta Polon. Pharm., 1865, vol. 22, No. 2, pp. 103–109.

Chemical Abstract, vol 60, No. 10, 1964, Abstract No. 60:11989d, "4 (or 5 or 6)–(2–Aminoalkyl) indols", FR, 1344579, Al.

Chemical Abstract, vol. 57, No. 10, 1962, Abstract No. 57:12438g, "Tryptamine Derivatives", GB 893707 A.

Chemical Abstract, vol. 55, No. 13, 1961, Abstract No. 55:12424a, "β–Aminoalkylthianaphthene and β–aminoalkylbenzofuran Derivatives", GB 855115 A.

* cited by examiner

RELEASE OF NORADRENALINE FROM ISOLATE BRAIN STEM ON ELECTRIC STIMULATION

● : STIMULATION

Antagonistic effect of compound No.3 in rats against tetrabenazine (T) induced depression of learning in the shuttle box Antagonistic effect of compound No.20 in rats against tetrabenazine (T) induced depression of learning in the shuttle box Antagonistic effect of compound No.25 in rats against tetrabenazine (T) induced depression of learning in the shuttle box Antagonistic effect of compound No.27 in rats against tetrabenazine (T) induced depression of learning in the shuttle box Enhancement of the slow inward Ca2+ current in sino-auricular fibers of frog hearts in Na-free Ringer (R) solution The effect of tyramine and the compounds of this invention on tritium release from synaptosomes incubated with $^3$H-DA, NA or 5-HT

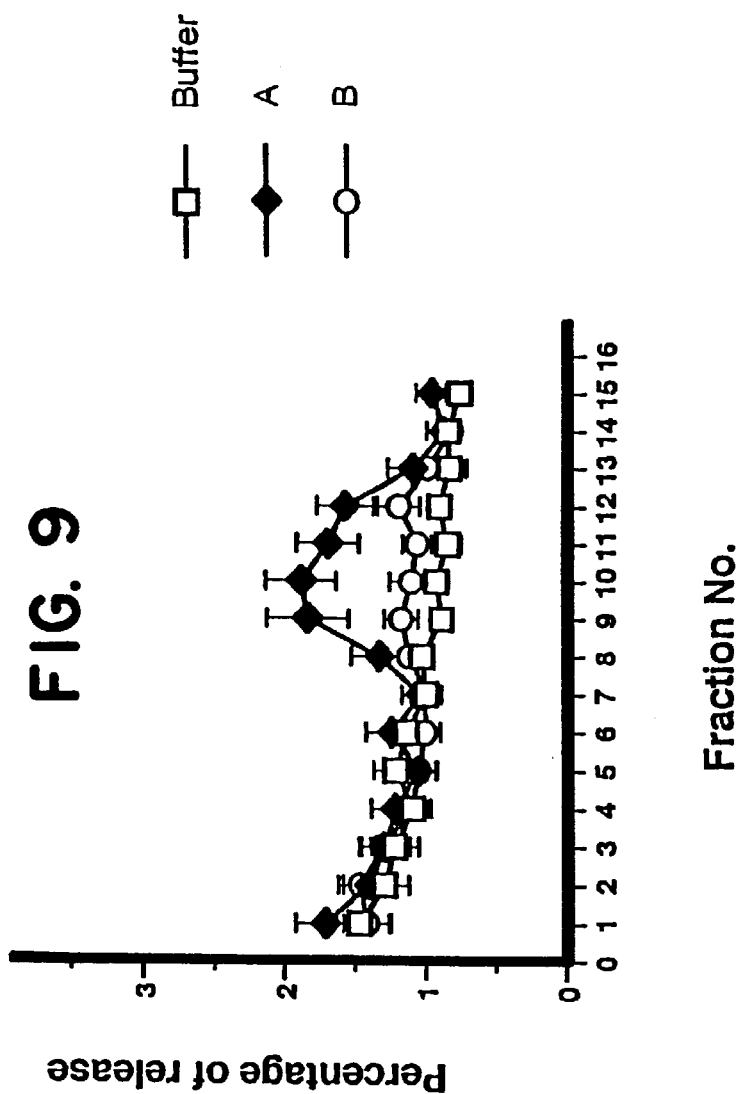

ETHYLAMINE DERIVATIVES

This application is a 371 of PCT/JP98/03468 Aug. 3, 1998.

BACKGROUND OF THE INVENTION

1. Field of the Invention

This invention relates to novel ethylamine derivatives which are promising as psychotropic drugs, antidepressants, drugs for Parkinson's disease and/or drugs for Alzimer's disease.

2. Description of the Related Art

A great many ethylamine derivatives have already been described in several publications. For example, 6-(2minoethyl)benzoxazolinone derivatives are described as antianxiety drugs and drugs for heart failure in EP 110, 781 and aminoalkylbenzoxazinone derivatives are described as useful remedies for damage of central nervous system in FR 2, 035,749. Moreover, the alkylamines which are structurally similar to the compounds of this invention are described as psychotropic drugs in JP examined publication 06-99, 420. However, as they have the releasing effects to displace catecholamines from their storage place on the central nervous system, they easily cause to release excess catecholamines from storage place such as synaptic vesicle and so on. Consequently, it is indicated that they have side effects as neurotoxicity similar to the effects of stimulants, abnormal behavior (excitation shown in high dose and the increase of intersignal reaction on conditioned avoidance task) or the like. The continuous administration of the drugs which enhance to release excess catecholamines cause decrease of catecholaminergic receptor. Consequently, the response of patients to drugs is reduced gradually and no sufficient therapeutic effect can be obtained as the result. Thus, they are inadequate as drugs for Parkinson's disease and Alzheimer's disease for which a long continuous treatment is required.

On the other hand, phenethylamine derivatives are disclosed in WO 88/2254 as psychotropic drugs and so on. These phenethylamine derivatives have the catecholaminergic activity enhancing effect (CAE effect: the enhancing effect on catecholamine release through amplification of the membrane potential dependent exocytosis) which is based on the new mechanism different from the above releasing effect to displace catecholamine from their storage [Life Sci., 58, 945–952 (1996)]. However, their compounds are not settled the effect which increase intersignal reaction on the conditioned avoidance task which is indicator of abnormal behavior. Therefore, the development of drugs which have high selectivity to CAE effect have been required.

The development of the compounds which have little side effects and are promising medicines as psychotropic drugs, antidepressant drugs, drugs for Parkinson's disease, drugs for Alzheimer's disease or the like has been longed for and an purpose of this invention is to comply with the said longing.

SUMMARY OF THE INVENTION

We, this inventors, judged that the neurotoxicity on central nervous system and abnormal behavior of said phenethylamine derivative are caused by or related to structural similarity with those of stimulants such as amphetamine and methamphetamine and bad examined diligently to achieve the purpose of this invention. As the result, we found out that certain kinds of specific novel ethylamine derivatives different from stimulants in structure and their acid addition salts had high selectivity to catecholaminergic activity enhancing effect (CAE effect), and completed this invention which was purposed to present psychotropic drugs, antidepressant drugs, drugs for Parkinson's disease and/or drugs for Alzheimer's disease which bad little side effects as neurotoxicity on central nervous system, abnormal behavior or the like.

This invention concerns with novel ethylamine derivatives of formula (I):

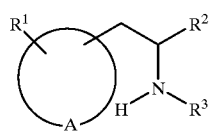

(I)

(wherein $R^1$ is hydrogen, hydroxyl, lower alkoxy or halogen; $R^2$ is alkyl having 2 to 5 carbon atoms; $R^3$ is hydrogen, alkyl having 2 to 5 carbon atoms, alkylcarbonyl having 2 to 5 carbon atoms, aryl having 6 to 10 carbon atoms or arylalkyl having 7 to 11 carbon atoms; the ring is a bicyclic compound which comprises of at least one benzene ring and may comprise a saturated or unsaturated five- or six-membered ring which may or may not have heteroatoms, providing that when the ring is indole or 1,3-benzodioxole, $R^2$ and $R^3$ do not constitute, at the same time, two carbon atoms members, and when $R^3$ is hydrogen, the ring is a bicyclic compound which is not indole, benzothiophene or benzodioxole and $R^2$ is alkyl having 3 to 5 carbon atoms) and pharmaceutically acceptable acid addition salts thereof. And this invention concerns with medicines as psychotropic drugs, antidepressants, drugs for Parkinson's disease, drugs for Alzheimer's disease or the like, wherein the active components are these compounds.

As the acid addition salts, they should preferably be pharmaceutically acceptable salts. Examples are salts with such inorganic acids as hydrochloric acid, sulfuric acid, hydrobromic acid, nitric acid, methanesulfonic acid or the like and salts with such organic acids as gluconic acid, tartaric acid, maleic acid, fumaric acid, succinic acid, malic acid, citric acid, mandelic acid or the like.

Lower alkoxy in formula (I) means the alkoxy having 1 to 4 carbon atoms. For example, it includes methoxy, ethoxy, n-propoxy, isopropoxy, n-butoxy, isobutoxy, tert-butoxy or the like.

Concrete examples of A ring are naphthalene, indole, 1,3-benzodioxole, 1,4-benzodioxane, indan, indene, benzofuran, benzothiophene, 2,3-dihydrobenzofuran, dihydronaphthalene, tetralin or the like. The substituents may be present in any positions in A ring.

stimulated points and ⌐: added points of compounds.

Figure 2:
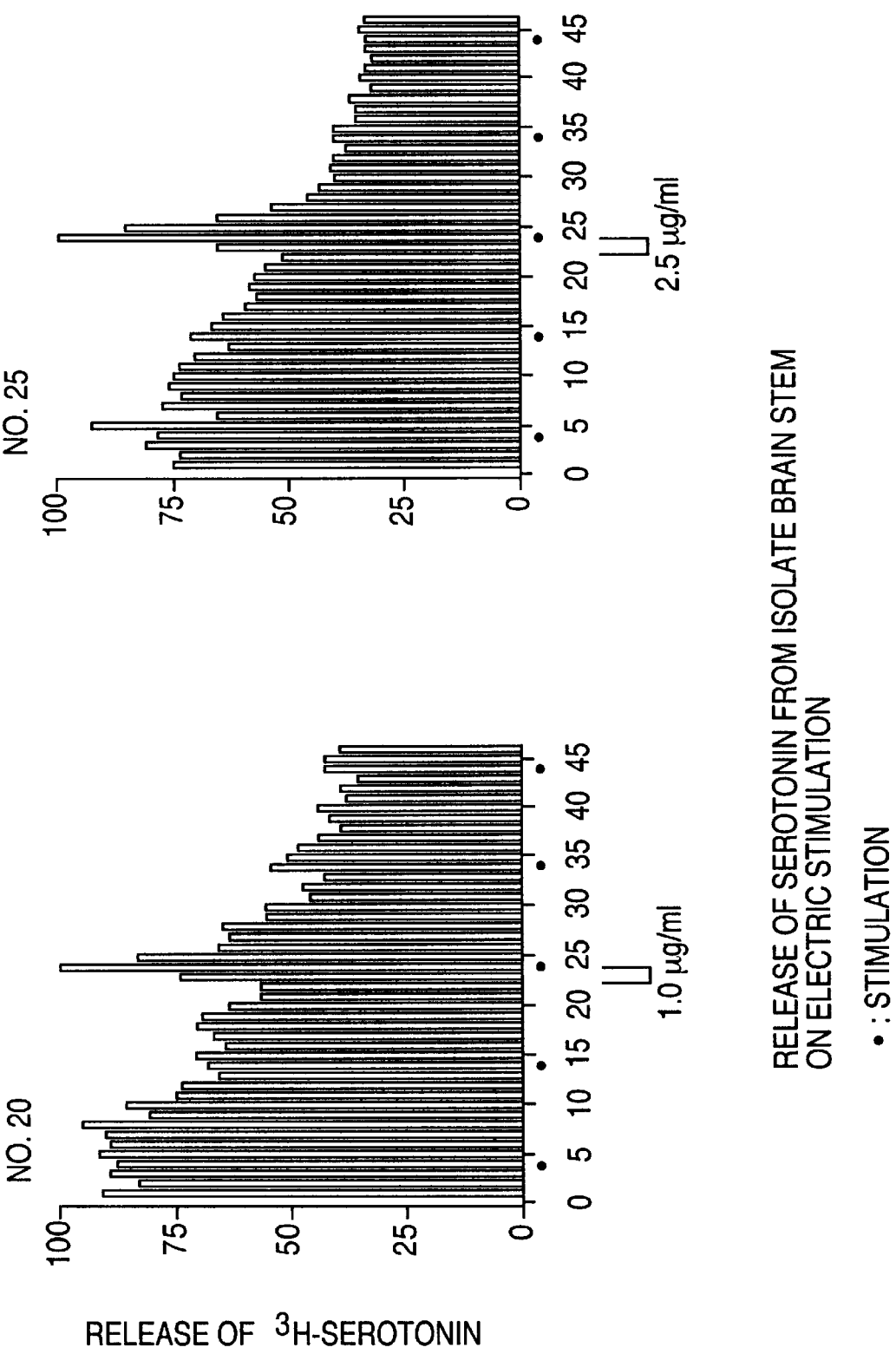

FIG. 2: Serotonin releasing effect of compounds Nos. 20 and 25 from electro stimulated isolated brain stem of rats.

stimulated points and ⌐: added points of compounds.

Figure 3:
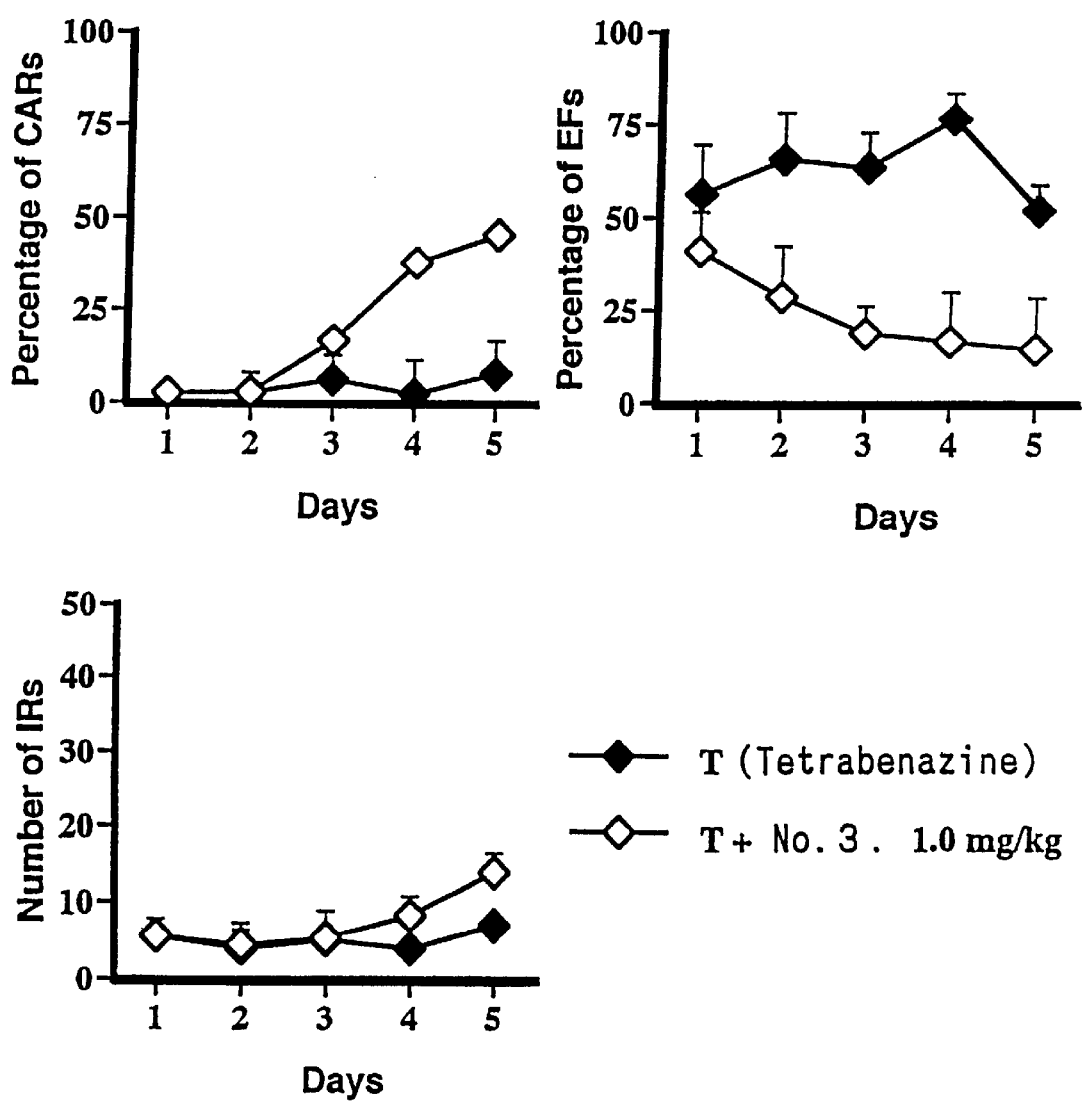

FIG. 3: Effect of compound No. 3 for conditioned avoidance reflex (CARs), escape failures (EFs) and intersignal reactions (IRs) of rats reduced learning ability by tetrabenazine.

Figure 4:
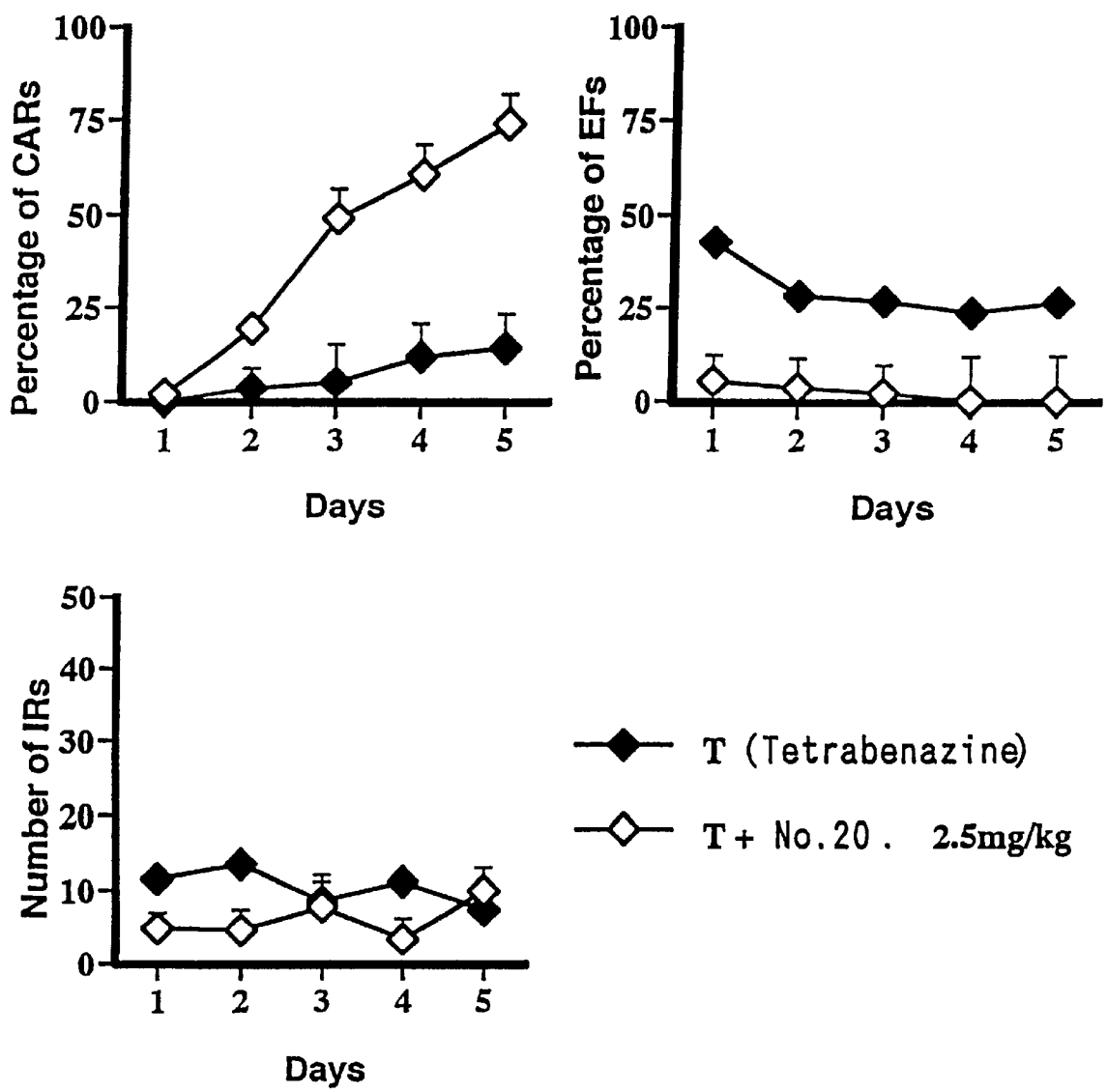

FIG. 4: Effect of compound No. 20 for conditioned avoidance reflex (CARs), escape failures (EFs) and inter-signal reactions (IRs) of rats reduced learning ability by tetrabenazine.

Figure 5:
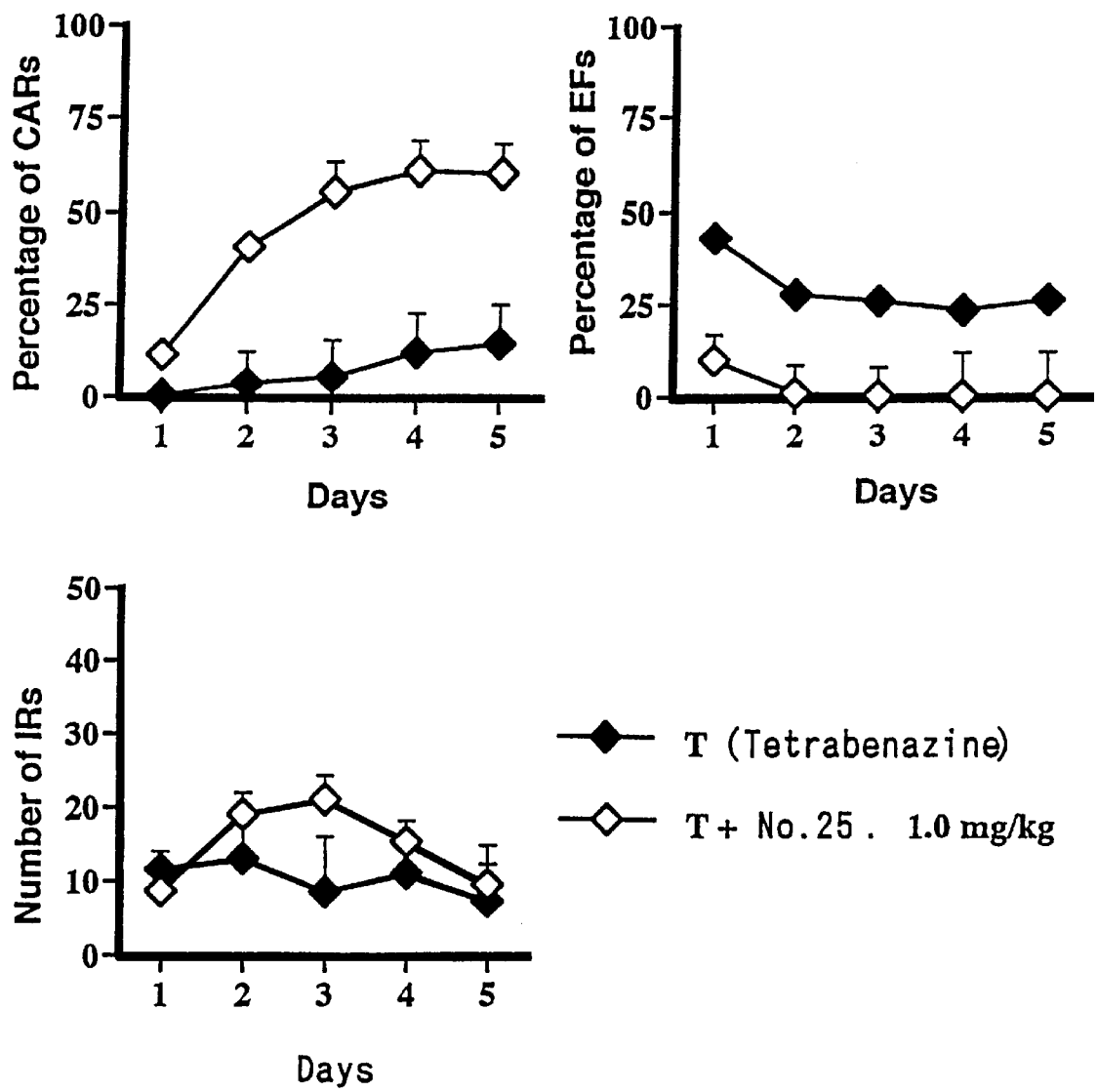

FIG. 5: Effect of compound No. 25 for conditioned avoidance reflex (CARs), escape failures (EFs) and inter-signal reactions (IRs) of rats reduced learning ability by tetrabenazine.

Figure 6:
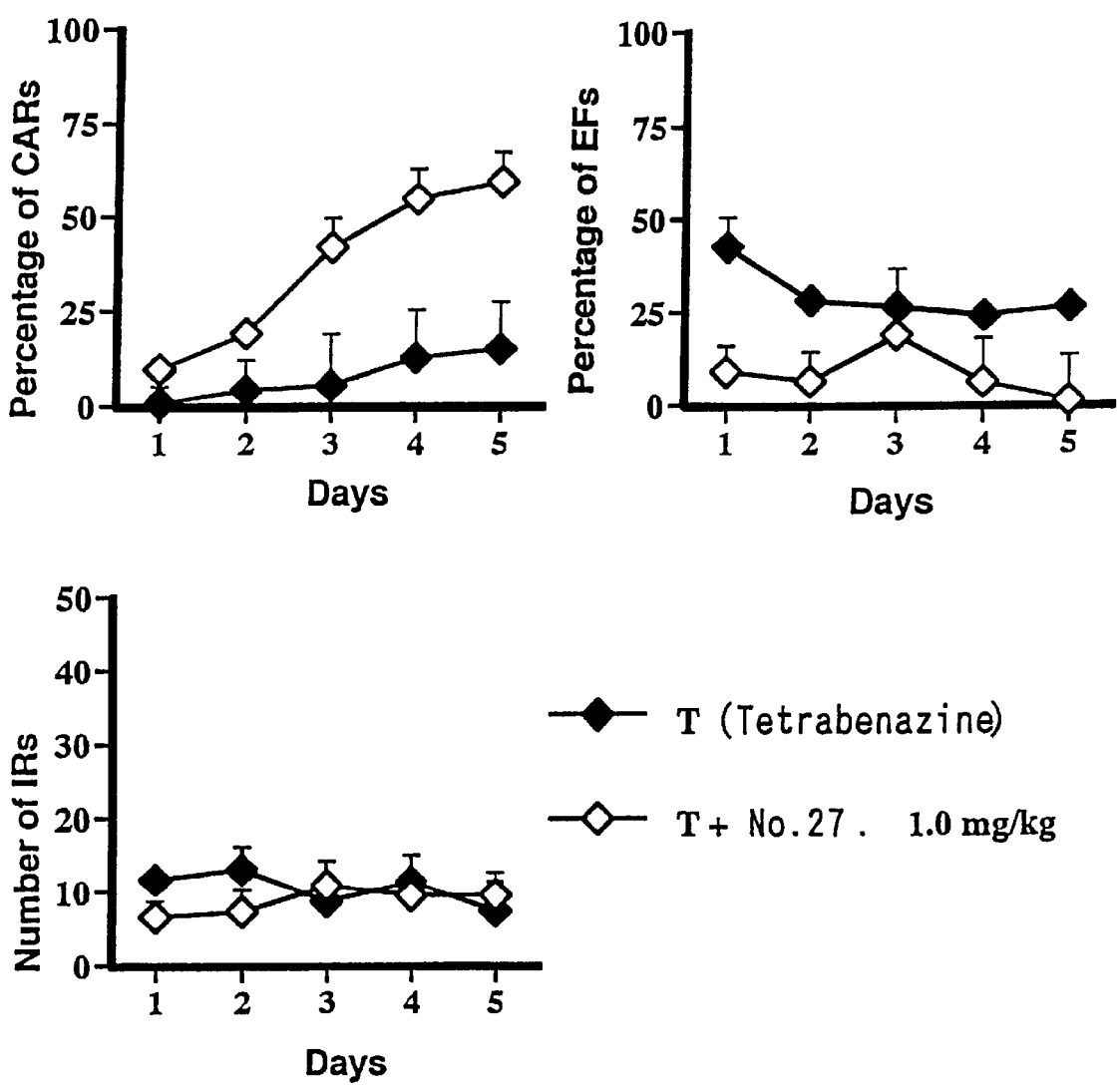

FIG. 6: Effect of compound No. 27 for conditioned avoidance reflex (CARs), escape failures (EFs) and inter-signal reactions (IRs) of rats reduced learning ability by tetrabenazine.

Figure 7:
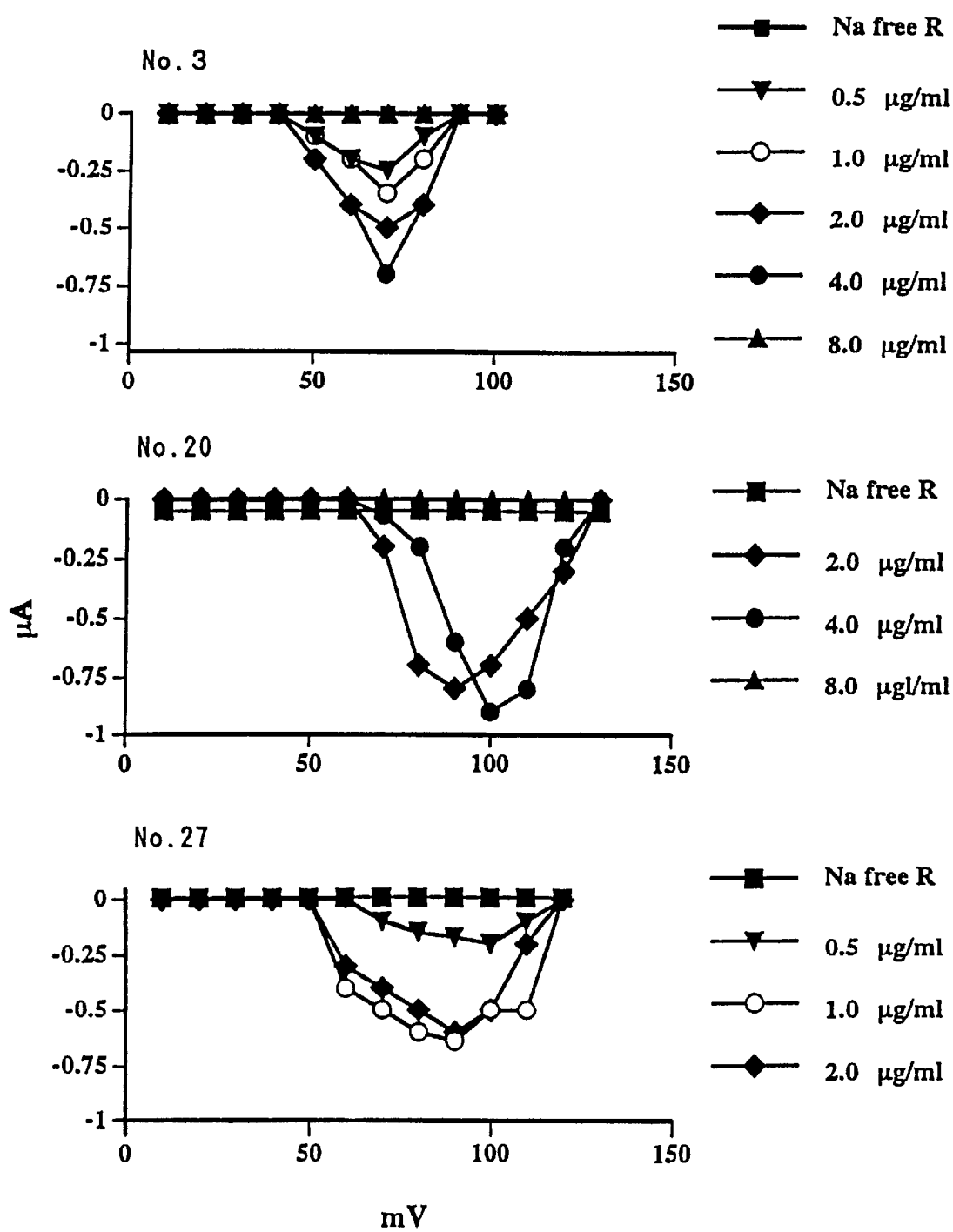

FIG. 7: Effect of compounds Nos. 3, 20 and 27 for the slow inward $Ca^{2+}$ current in sin-oauricular fibers of frog hearts.

Figure 8:
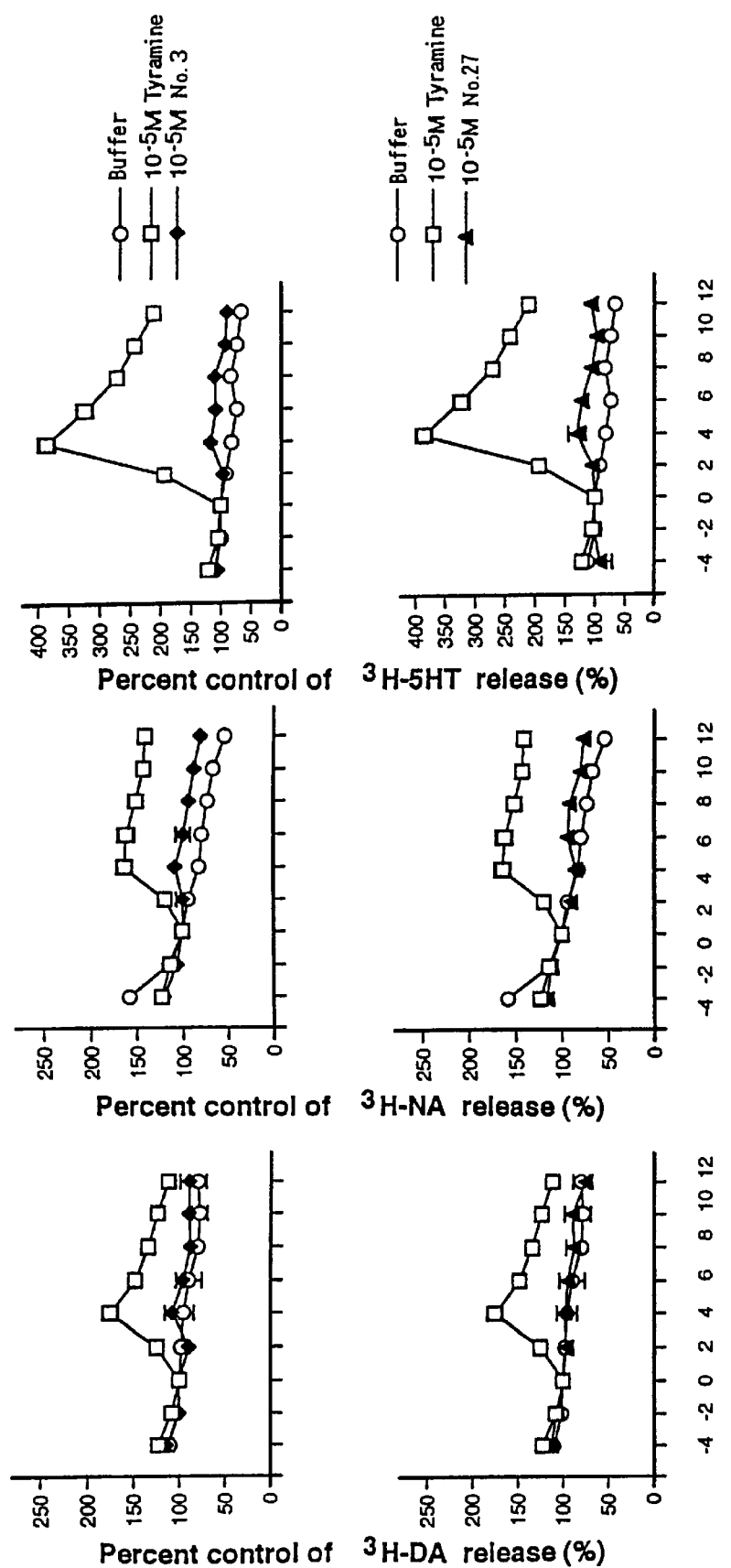

FIG. 8: Effect of compounds Nos. 3 and 27 for monoamine release from synaptosome.

FIG. 9: Tyramine antagonistic property of compound No. 27; A: Tyramine ($10^{-6}$ M) was added from fraction No. 8 to 12, B: Compound No. 27 ($5 \times 10^{-5}$ M) was added from fraction No. 4 to 12 and tyramine ($10^{-6}$ M) was added from fraction No. 8 to 12.;

DESCRIPTION OF THE PREFERRED EMBODIMENTS

Particularly preferable compounds represented by formula (I) are 1-(2-Naphthyl)-2-propylaminopentane, 1-(Indol-3-yl)-2-propylaminopentane, 1-(Benzofuran-2-yl)-2-propylaminopentane, 1-(Benzodioxol-5-yl)-2-propylaminopentane or 1-(Benzodioxol-4-yl)-2-propylaminopentane.

All of the compounds of this invention are not described in any previous literature and can be prepared by the following methods.

[Route 1]

Nitro compounds of formula (II):

(II)

(wherein $R^1$ is hydrogen, hydroxyl, lower alkoxy or halogen; $R^2$ is alkyl having 2 to 5 carbon atoms; the ring is a bicyclic compound which comprises of at least one benzene ring and may comprise a saturated or unsaturated five- or six-membered ring which may or may not have heteroatoms) and reductant like lithium aluminum hydride are reacted in an inert solvent like tetrahydrofuran (THF) for 1 to 200 hr at a temperature ranging room from temperature to reflux temperature to obtain amine compounds of formula (III):

(III)

(wherein $R^1$, $R^2$ and the ring are of the same meaning as defined above formula (I)).

Among the amine compounds obtained by this process, the compounds, wherein the ring is a bicyclic compound which is not indole, benzothiophene or benzodioxole and $R^2$ is alkyl having 3 to 5 carbon atoms, constitute a part of the novel compounds of this invention. These amine compounds as well as the other compounds of formula (III) can be utilized as intermediates to prepare other novel compounds of this invention.

In this invention, the above mentioned compounds of the formula (III) are, as desired, reacted with an acid halides of the formula (IV):

(IV)

(wherein $R^4$ is alkyl having 1 to 4 carbon atoms or aryl having 6 to 10 carbon atoms; X is halogen) in the presence of basic condensing agent like triethylamine or pyridine in an inert solvent like THF, chloroform, carbon tetrachloride or the like for 1 to 48 hr at a temperature ranging from room temperature to reflux temperature, to obtain compounds of formula (V):

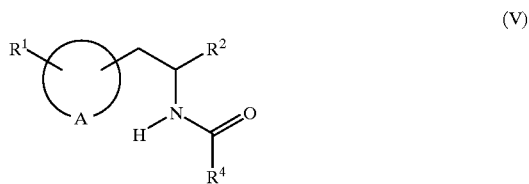

(V)

(wherein $R^1$, $R^2$, $R^4$ and the ring are of the same meaning as above defined).

Thus obtained compounds, wherein $R^4$ is alkyl having 1 to 4 carbon atoms, constitute a part of the present novel compounds of this invention. These compounds as well as other compounds of formula (V) can be utilized as intermediates to prepare other novel compounds of this invention. However, among the compounds of formula (V) wherein $R^4$ is alkyl having 1 to 4 carbon atoms, the compounds wherein the ring is indole or 1,3-benzodioxole, $R^2$ is alkyl having two carbon atoms, i.e. ethyl, and $R^3$ can not have one carbon atom, i.e. methyl, are omitted as beyond the limits of this invention As desired, in the present invention, these compounds of above formula (V) and reductants like lithium aluminum hydride or aluminum hydride are reacted in an inert solvent like THF or ether, for 1 to 48 hr at a temperature ranging from room temperature to reflux temperature, to obtain the novel ethylamine derivatives of formula (I).

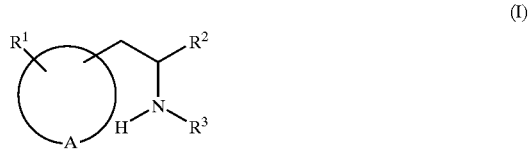

(I)

Furthermore, these ethylamine compounds are led to their pharmaceutically acceptable salts as desired.

Therefore, among the compounds of this invention of formula (I) obtained by the method of route 1, $R^1$ is hydrogen, hydroxyl, lower alkoxy or halogen; $R^2$ is alkyl having 2 to 5 carbon atoms; $R^3$, which shows concretely all kinds of substituents on amino nitrogen atom of the products obtained by the above each process, is hydrogen, alkyl having 2 to 5 carbon atoms, alkylcarbonyl having 2 to 5 carbon atoms or arylalkyl having 7 to 11 carbon atoms; the ring is a bicyclic compound which comprises of at least one benzene ring and may comprise a saturated or unsaturated five- or six-membered ring which may or may not have heteroatoms, providing that when the ring is indole or 1,3-benzodioxole, $R^2$ and $R^3$ do not constitute, at the same time, two carbon atoms members, and when $R^3$ is hydrogen, the ring is a bicyclic compound than indole and benzo[b] thiopene or benzodioxole and $R^2$ is alkyl having 3 to 5 carbon atoms.

The compounds of formula (II) used as starting materials in the route 1 method can be synthesized by the method described in Journal of Medicinal Chemistry, 35, 280–285 (1992). That is, a compound of the formula (VI):

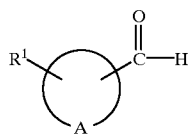
(VI)

(wherein $R^1$ and the ring are of same meaning as defined above formula (I)) is condensed with nitroalkane to obtain the compounds of general formula (II).

[Route 2]

Furthermore, the compounds of this invention can be advantageously prepared by the following method of route 2. That is, a ketone compound of formula (VII):

(VII)

(wherein $R^1$ is hydrogen, hydroxyl, lower alkoxy or halogen; $R^2$ is alkyl having 2 to 5 carbon atoms; the ring is a bicyclic compound which consists of at least one benzene ring and may comprise a saturated or unsaturated five- or six-membered ring which may or may not have heteroatoms) is reacted with an amine compound of formula (VIII):

$R^3$—$NH_2$ (VIII)

(wherein $R^3$ is alkyl having 2 to 5 carbon atoms, aryl having 6 to 10 carbon atoms or arylalkyl having 7 to 11 carbon atoms) in the presence of reductant like sodium triacetoxyborohydride, sodium borohydride or lithium aluminum hydride, in an inert solvent like THF, dichloromethane or 1,2-dichloroethane, for 1 to 200 hr at a temperature ranging from room temperature to reflux temperature to obtain an ethylamine derivative of formula (I).

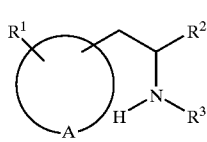
(I)

According to this method, it is possible to obtain the compounds of formula (I), wherein $R^1$ is hydrogen, hydroxyl, lower alkoxy or halogen; $R^2$ is alkyl having 2 to 5 carbon atoms; $R^3$ is hydrogen, alkyl having 2 to 5 carbon atoms, aryl having 6 to 10 carbon atoms or arylalkyl having 7 to 11 carbon atoms; the ring is a bicyclic compound which comprise of at least one benzene ring and may contain a saturated or unsaturated five- or six-membered ring which may or may not have heteroatoms. However the invention excludes the compound of formula (I) wherein the ring is indole or 1,3-benzodioxole and $R^2$ and $R^3$ represent, at the same time, two carbon atoms members.

The compounds of formula (VII) which are starting materials can be synthesized by the method described in Journal of Medicinal Chemistry, 29, 2009–2015 (1986).

The compounds of this invention and acid addition salts thereof have the CAE effect. Therefore, they enhance catecholamine release in modulatory. Accordingly, they can be used as medicines which are effective as drugs for Parkinson's disease, antidepressants, psychotropic drugs, drugs for Aizheimer's disease or the like and have little side effects.

The compounds of this invention does not have the effects which usually appear in the conventional drugs for Parkinson's disease, antidepressants or the like. That is, their compounds does not hove monoamine oxidase inhibitory effect, catecholamine uptake inhibitory effect, the releasing effect to displace catecholamines from their storage place, affinity to various receptors on nerve cell and so on. However, these compounds significantly improved reduced learning ability of rats injected with catecholamine depletor tetrabenazine. The action of the compounds of this invention is based on CAE effect, which is the modulated physiologically enhancing effect of catecholamine release through amplification of membrane potential dependent exocytosis (i.e. the increase of the stimulant related between action potential and release of transmitter). Following pharmacological experiments, specifically described in Examples 30–32, revealed that the compounds of this invention had highly selective CAE effects. That is, it confirmed that the compounds of this invention did not have the releasing effect to displace catecholamines from their storage place, the monoamine oxidase inhibitory effect and the affinity to various receptors on nerve cell. Furthermore, the compounds of this invention caused the increase of the slow inward $Ca^{2+}$ currents in the sinoauricular fibers of the frog heart. Then amounts of catecholamines released from the rat brain stem were measured on resting potential and electrostimulation, the compounds of this invention did not change them on the resting potential but significantly increased them by the electrostimulation. These results show that the compounds of this invention have CAE effect.

CAE effect is the enhancing effect of catecholamine release through amplification of the membrane potential dependent exocytosis as mentioned above and is following the physiological mechanism in which the efficacy is displayed in response to the action potential. So this mechanism is quite different from usual monoamine oxidase inhibitors, catecholamine uptake inhibitors, amphetamine-like stimulants and the phenethylamine-like releasors to displace catecholamines from their storage place. Then the compounds of this invention have the specific spectra of actions which do not have the release of excess catecholamines, the sudden increase to their high concentration and the induction to depletion of catecholamines on neuroterminals. Consequently, the compounds of this invention are hard to cause the decrease and the damage of catecholaminergic receptor under the existing excess catecholamines. Therefore, the compounds of this invention decrease little the response to patients and have little side effects which are the increase of abnormal behavior (excitation), neurotoxicity on central nerve and so on. Consequently, the compounds of this invention have high safety and better efficacy as antidepressants, psychotropic drugs, drugs for Parkinson's disease, drugs for Alzheimer's disease and so on. Thus, the compounds of this invention are useful as compounds which keep their efficacy by continuous treatment for long term.

When the compounds of this invention and their pharmaceutically acceptable acid addition salts are used as medicines, these compounds are usually mixed with carrier, vehicle, dilution, solubilizer or the like. And these compounds can be administered orally or parenterally as tablets, powders, granules, capsules, syrups, injections or the like. The adult oral dose of these compounds is usually between 0.1 and 100 mg/day and they are administered once or several times a day. However these doses can be changed by conditions, age, body weight or the like of patients.

The compounds of this invention are more concretely stated hereinbelow. But it goes without saying that this invention is not limited to them.

EXAMPLE 1

Synthesis of 1-(2-Naphthyl)-2-aminopentane Hydrochloride (compound No. 1)

A solution of 7.70 g (31.9 mmol) of 1-(2-naphthyl)-2-nitro-1-pentene in tetrahydrofuran (THF) (30 ml) was added dropwise to a suspension of 2.42 g (63.8 mmol) of lithium aluminum hydride (LiAlR$_4$) in THF (40 ml) over 1 hr under ice cooling and the mixture was stirred overnight at room temperature. After excessive LiAlH$_4$ was decomposed with distilled water under ice cooling the mixture was filtered and the filtrate was concentrated. Thereafter, ether (100 ml) was added to the concentrate and was extracted three times with 0.5 N hydrochloric acid (50 ml). The obtained water phase was alkalized with 28% aqueous ammonia and was extracted three times with ether (100 ml). The obtained organic phase was dried over anhydrous sodium sulfate, concentrated and purified by flash column chromatography. A mixture of chloroform/methanol (10:1) was used for eluting solvent, 1-(2-naphthyl)-2-aminopentane was obtained to yield 5.36 g (79%) as light yellow oil.

The above oil was dissolved in anhydrous ether and was converted to hydrochloride with the ether solution saturated with hydrochloric acid.

| m.p. | 175.0–177.0° C. |
|---|---|
| MS | 214 [M + 1]$^+$ (m/z) |
| NMR (CDCl$_3$) | 0.60–1.20 (3H, m), 1.30–2.10 (4H, m), 2.50–4.00 (3H, m), 7.20–8.10 (7H, m), 8.20–9.30 (3H, br) |
| IR | 2950, 2910, 1585, 1500, 820, 760 (cm$^{-1}$) |

Elementary analysis: as C$_{15}$H$_{19}$N.HCl

| Calcld. | C: 72.12, H: 8.07, N: 5.61 (%) |
|---|---|
| Found | C: 72.11, H: 8.06, N: 5.45 (%) |

EXAMPLE 2

Synthesis of N-[2-(1-(2-naphthyl))pentyl] propionamide (compound No. 2)

To an anhydrous THF (40 ml) solution of mixture of 5.36 g (25.1 mmol) of 1-(2-naphthyl)-2-amino-pentane obtained by Example 1 and 3.81 g (37.7 mmol) of triethylamine a solution of 4.64 g (50.1 mmol) of propionyl chloride in anhydrous THF (10 ml) was added dropwise under 0° C. The mixture was stirred overnight at room temperature and was concentrated. The condensate was washed with 5% hydrochloric acid, 5% sodium carbonate and saturated sodium chloride solution. The crude product was dried over anhydrous sodium sulfate, concentrated and purified by flash column chromatography. A mixture of chloroform/hexane (5:2) was used for eluting solvent. N-[2-(1-(2-naphthyl)) pentyl]-propionamide was recrystallized from ether-hexane to yield 5.48 g (81.0%) as white crystal.

| m.p. | 92.0° C. |
|---|---|
| MS | 269 [M]$^+$ (m/z) |
| NMR (CDCl$_3$) | 0.70–1.27 (6H, m), 1.27–1.85 (4H, m), 2.10 (2H, q, J = 7.8 Hz), 2.93 (2H, d, J = 7.2 Hz), 3.90–4.75 (1H, br), 5.20–5.75 (1H, m), 7.20–8.10 (7H, m) |
| IR | 3280, 2950, 1640, 1540 (cm$^{-1}$) |

Elementary analysis: as C$_{18}$H$_{23}$NO

| Calcld. | C: 80.26, H: 8.61, N: 5.20 (%) |
|---|---|
| Found | C: 80.09, H: 8.57, N: 5.15 (%) |

EXAMPLE 3

Synthesis of 1-(2-Naphthyl)-2-propylaminopentane Hydrochloride (compound No. 3)

2.70 g (71.1 mmol) of LiAlH$_4$ were suspended in 30 ml of anhydrous ether and a solution of 2.71 g (20.3 mmol) anhydrous aluminum chloride in anhydrous ether (20 ml) was added dropwise thereto under ice cooling to prepare an anhydrous ether solution of aluminum hydride. To this, a solution of N-[2-(1-(2-naphthyl))pentyl]propionamide (5.48 g, 20.3 mmol) obtained in Example 2 in anhydrous ether (40 ml) was added dropwise under ice cooling and the mixture was stirred at 0° C. for a while and then stirred overnight at room temperature. After reaction, distilled water was added to the mixture little by little. The mixture was alkalized with 5 N sodium hydroxide, filtered and the filtrate was concentrated. Thereafter, ether (100 ml) was added to the concentrate and the mixture was extracted four times with 0.5 N hydrochloric acid (70 ml). Thus obtained water phase was alkalized with 28% aqueous ammonia and extracted three times with ether (100 ml). The obtained organic phase was dried over anhydrous sodium sulfate, concentrated and purified by flash column chromatography. A mixture of chloroform/metha nol (30:1) was used for eluting solvent.

2.40 g of 1-(2-Naphthyl)-2-propylaminopentane were obtained (46% yield) as light yellow oil.

Using the same method as stated in Example 1, 1-(2-naphthyl)-2-propylaminopentane was converted to hydrochloride.

| m.p. | 181.5–182.5° C. |
|---|---|
| MS | 256 [M + 1]$^+$ (m/z) |
| NMR(CDCl$_3$) | 0.95 (6H, t, J = 7.0 Hz), 1.15–2.40 (6H, m), 2.60–4.00 (5H, m), 7.25–8.10 (7H, m), 9.30–10.15 (2H, br) |
| IR | 2975, 2880, 2800, 2750, 1595, 1465, 765 (cm$^{-1}$) |

Elementary analysis: as C$_{18}$H$_{25}$N.HCl

| Calcld. | C: 74.07, H: 8.98, N: 4.80 (%) |
|---|---|
| Found | C: 73.98, H: 8.94, N: 4.87 (%) |

EXAMPLE 4

Synthesis of 1-(2-Naphthyl)-2-propylaminopentane Maleic Acid Salt (compound No. 4)

To 0.7 g (2.7 mmol) of 1-(2-naphthyl)-2-propylaminopentane obtained by Example 3, a solution of 0.15 g (1.3 mmol) of maleic acid in ethanol (2 ml) was added. The mixture was kept stand at about 5° C. The precipitated product was filtered and 1-(2-Napthyl)-2-propyl-aminopentane maleic acid salt was obtained (0.33 g, yield 32%).

| m.p. | 84.0–85.5° C. |
|---|---|
| MS | 256 [M + 1]$^+$ (m/z) |
| NMR(CDCl$_3$) | 0.92 (6H, t, J = 6.0 Hz), 1.15–2.20 (6H, m), 2.75–3.90 (5H, m), 6.24 (2H, s), 7.15–8.10 (7H, m) |
| IR | 2980, 2890, 2820, 2770, 1600, 1520, 1405, 1380, 880 (cm$^{-1}$) |

Elementary analysis: as C$_{18}$H$_{25}$N.C$_4$H$_4$O$_4$

| Calcld. | C: 71.13, H: 7.87, N: 3.77 (%) |
|---|---|
| Found | C: 71.30, H: 7.92, N: 3.77 (%) |

EXAMPLE 5

The compound obtained by Example 1 or its derivatives were reacted with acid chloride. Using the same procedures as stated in Examples 2 and 3, the corresponding ethylamine derivatives were obtained as hydrochlorides; compounds No. 5–17 shown in Table 1, and the physicochemical data of the above compounds No. 5–17 were shown in Tables 2 and 3.

TABLE 1

Compounds No. 5–17

| Compound No. | A ring | R$^1$ | R$^2$ | R$^3$ | Yield (%) |
|---|---|---|---|---|---|
| Compound No. 5 | 1-Naphthyl | H | —CH$_2$CH$_2$CH$_3$ | —CH$_2$CH$_2$CH$_3$ | 43 |
| Compound No. 6 | 2-Naphthyl | H | —CH$_2$CH$_2$CH$_3$ | —CH$_2$CH$_3$ | 33 |
| Compound No. 7 | 2-Naphthyl | H | —CH$_2$CH$_2$CH$_3$ | —CH$_2$CH$_2$CH$_2$CH$_3$ | 39 |
| Compound No. 8 | 2-Naphthyl | H | —CH$_2$CH$_2$CH$_3$ | —CH$_2$CH(CH$_3$)$_2$ | 28 |
| Compound No. 9 | 2-Naphthyl | H | —CH$_2$CH$_2$CH$_3$ | —CH$_2$CH$_2$CH$_2$CH$_2$CH$_3$ | 39 |
| Compound No. 10 | 2-Naphthyl | H | —CH$_2$CH$_3$ | —CH$_2$CH$_2$CH$_3$ | 46 |
| Compound No. 11 | 2-Naphthyl | H | —CH$_2$CH$_2$CH$_2$CH$_3$ | —CH$_2$CH$_2$CH$_3$ | 52 |
| Compound No. 12 | 2-Naphthyl | H | —CH$_2$CH$_2$CH$_2$CH$_2$CH$_3$ | —CH$_2$CH$_2$CH$_3$ | 30 |
| Compound No. 13 | 2-Naphthyl | H | —CH$_2$CH$_2$CH$_3$ | —CH$_2$CH$_2$CH(CH$_3$)$_2$ | 26 |
| Compound No. 14 | 2-Naphthyl | H | —CH$_2$CH$_2$CH$_3$ | —CH$_2$C(CH$_3$)$_3$ | 38 |
| Compound No. 15 | 2-Naphthyl | 6-OCH$_3$ | —CH$_2$CH$_2$CH$_3$ | —CH$_2$CH$_2$CH$_3$ | 32 |
| Compound No. 16 | 1-Naphthyl | 4-OCH$_3$ | —CH$_2$CH$_2$CH$_3$ | —CH$_2$CH$_2$CH$_3$ | 37 |
| Compound No. 17 | 1-Naphthyl | 2-OCH$_3$ | —CH$_2$CH$_2$CH$_3$ | —CH$_2$CH$_2$CH$_3$ | 14 |

TABLE 2

Physicochemical properties of compounds No. 5–11

Compound 5
| m.p. (° C.) | 107.5 . 109.0 |
|---|---|
| MS (m/z) | 256 [M+1]$^+$ |
| NMR (CDCl$_3$: δ) | 0.92(6H, t, J=8.0Hz), 1.10–2.45(6H, m), 2.45–3.20(2H, br), 3.20–4.50(3H, m), 7.25–8.45(7H, m), 9.20–10.15(2H, br) |
| IR (cm$^{-1}$) | 2960, 2870, 2800, 2750, 770 |

Elementary analysis (%): as C$_{18}$H$_{25}$N.HCl
| Calcld. | C: 74.07, H: 8.98, N: 4.80 |
|---|---|
| Found | C: 73.67, H: 8.87, N: 4.69 |

Compound No. 6
| m.p. (° C.) | 165.0–165.5 |
|---|---|
| MS (m/z) | 242 [M+1]$^+$ |
| NMR (CDCl$_3$: δ) | 0.65–1.10(3H, m), 1.10–2.30(7H, m), 2.65–4.10(5H, m), 7.25–8.10(7H, m), 9.25–10.15(2H, br) |
| IR (cm$^{-1}$) | 2960, 2830, 2800, 2740, 1565, 1455, 760 |

Elementary analysis (%): as C$_{17}$H$_{23}$N.HCl
| Calcld. | C: 73.49, H: 8.71, N: 5.04 |
|---|---|
| Found | C: 73.26, H: 8.55, N: 4.96 |

Compound No. 7
| m.p. (° C.) | 141.5–142.5 |
|---|---|
| MS (m/z) | 270 [M+1]$^+$ |
| NMR (CDCl$_3$: δ) | 0.65–1.15(6H, m), 1.15–2.35(8H, m), 2.50–4.00(5H, m), 7.30–8.10(7H, m), 9.30–10.15(2H, br) |
| IR (cm$^{-1}$) | 2960, 2870, 2770, 2730 |

Elementary analysis (%): as C$_{19}$H$_{27}$N.HCl
| Calcld. | C: 74.60, H: 9.23, N: 4.58 |
|---|---|
| Found | C: 74.34, H: 9.09, N: 4.50 |

Compound No. 8
| m.p. (° C.) | 156.5–157.5 |
|---|---|
| MS (m/z) | 270 [M+1]$^+$ |

TABLE 2-continued

Physicochemical properties of compounds No. 5–11

| | |
|---|---|
| NMR (CDCl$_3$: δ) | 0.60–1.25(9H, m), 1.25–2.10(4H, m), 2.10–3.05(3H, m), 3.05–4.00(3H, m), 7.30–8.00(7H, m), 9.20–10.00(2H, br) |
| IR (cm$^{-1}$) | 2960, 2860, 2790, 1585, 1470 |
| Elementary analysis (%): as C$_{19}$H$_{27}$N.HCl | |
| Calcld. | C: 74.60, H: 9.23, N: 4.58 |
| Found | C: 74.36, H: 9.08, N: 4.42 |

Compound No. 9
| | |
|---|---|
| m.p. (° C.) | 106.5–107.5 |
| MS (m/z) | 284 [M+1]$^+$ |
| NMR (CDCl$_3$: δ) | 0.50–1.05(6H, m), 1.05–2.35(10H, m), 2.45–4.00(5H, m), 7.30–8.05(7H, m), 9.15–10.15(2H, br) |
| IR (cm$^{-1}$) | 2950, 2850, 1575, 1450, 810, 745, 475 |
| Elementary analysis (%): as C$_{20}$H$_{29}$N.HCl | |
| Calcld. | C: 75.09, H: 9.45, N: 4.38 |
| Found | C: 74.78, H: 9.23, N: 4.22 |

Compound 10
| | |
|---|---|
| m.p. (° C.) | 180.5–182.0 |
| MS (m/z) | 242 [M+1]$^+$ |
| NMR (CDCl$_3$: δ) | 0.95(3H, t, J=7.0Hz), 1.07(3H, t, J=7.0Hz), 1.50–2.50(4H, m), 2.60–4.00(5H, m), 7.25–8.05(7H, m), 9.20–10.15(2H, br) |
| IR (cm$^{-1}$) | 2960, 2800, 2750, 1600, 1590, 1460, 820, 760 |
| Elementary analysis (%): as C$_{17}$H$_{23}$N.HCl | |
| Calcld. | C: 73.49, H: 8.71, N: 5.04 |
| Found | C: 73.39, H: 8.60, N: 4.83 |

Compound No. 11
| | |
|---|---|
| m.p. (° C.) | 124.5–126.5 |
| MS (m/z) | 270 [M+1]$^+$ |
| NMR (CDCl$_3$: δ) | 0.65–2.45(14H, m), 2.60–4.00(5H, m), 7.30–8.10(7H, m), 9.30–10.15(2H, br) |
| IR (cm$^{-1}$) | 2950, 2860, 2790, 810 |
| Elementary analysis (%): as C$_{19}$H$_{27}$N.HCl | |
| Calcld. | C: 74.60, H: 9.23, N: 4.58 |
| Found | C: 74.40, H: 9.08, N: 4.43 |

TABLE 3

Physicochemical properties of compounds No. 12–17

Compound No. 12
| | |
|---|---|
| m.p. (° C.) | 116.0–117.5 |
| MS (m/z) | 284 [M+1]$^+$ |
| NMR (CDCl$_3$: δ) | 0.50–2.50(16H, m), 2.50–4.00(5H, m), 7.20–8.10(7H, m), 9.30–10.15(2H, br) |
| IR (cm$^{-1}$) | 3420, 2950, 2850, 2790 |
| Elementary analysis (%): as C$_{20}$H$_{29}$N.HCl | |
| Calcld. | C: 75.09, H: 9.45, N: 4.38 |
| Found | C: 74.95, H: 9.30, N: 4.31 |

Compound No. 13
| | |
|---|---|
| m.p. (° C.) | 144.5–146.0 |
| MS (m/z) | 284 [M+1]$^+$ |
| NMR (CDCl$_3$: δ) | 0.50–1.15(9H, m), 1.15–2.20(7H, m), 2.40–4.10(5H, m), 7.25–8.20(7H, m), 9.25–10.15(2H, br) |
| IR (cm$^{-1}$) | 2950, 2850, 2770, 1460 |
| Elementary analysis (%): as C$_{20}$H$_{29}$N.HCl | |
| Calcld. | C: 75.09, H: 9.45, N: 4.38 |
| Found | C: 74.87, H: 9.28, N: 4.03 |

| | |
|---|---|
| m.p. (° C.) | 159.0–161.0 |
| MS (m/z) | 284 [M+1]$^+$ |
| NMR (CDCl$_3$: δ) | 0.60–1.00(3H, m), 1.25(9H, s), 1.40–2.20(4H, m), 2.40–3.30(3H, m), 3.40–4.30(2H, m), 8.25–8.00(7H, m), 9.00–10.00(2H, br) |
| IR (cm$^{-1}$) | 2940, 2850 |
| Elementary analysis (%): as C$_{20}$H$_{29}$N.HCl | |
| Calcld. | C: 75.09, H: 9.45, N: 4.38 |
| Found | C: 74.66, H: 9.27, N: 4.18 |

Compound No. 15
| | |
|---|---|
| m.p. (° C.) | 186.0–186.5 |
| MS (m/z) | 286 [M+1]$^+$ |
| NMR (CDCl$_3$: δ) | 0.95(6H, t, J=7.0Hz), 1.20–2.45(6H, m), 2.50–3.85(5H, m), 3.90(3H, s), 6.95–7.95(6H, m), 9.10–10.15(2H, br) |

TABLE 3-continued

Physicochemical properties of compounds No. 12–17

| | |
|---|---|
| IR (cm$^{-1}$) | 2960, 2930, 2860, 2770, 1455, 1265, 1230, 1030 |
| Elementary analysis (%): as C$_{19}$H$_{27}$NO.HCl | |
| Calcld. | C: 70.90, H: 8.77, N: 4.35 |
| Found | C: 70.68, H: 8.58, N: 4.36 |

Compound No. 16
| | |
|---|---|
| m.p. (° C.) | 188.0–190.0 |
| MS (m/z) | 286 [M+1]$^+$ |
| NMR (CDCl$_3$: δ) | 0.92(6H, t, J=7.0Hz), 1.15–2.45(6H, m), 2.50–3.80(5H, m), 3.97(3H, s), 6.55–8.50(6H, m), 9.25–10.15(2H, br) |
| IR (cm$^{-1}$) | 2950, 2860, 2770, 1585, 1390, 1270, 1090 |
| Elementary analysis (%): as C$_{19}$H$_{27}$NO.HCl | |
| Calcld. | C: 70.90, H: 8.77, N: 4.35 |
| Found | C: 70.53, H: 8.60, N: 4.38 |

Compound No. 17
| | |
|---|---|
| m.p. (° C.) | 133.5–135.0 |
| MS (m/z) | 286 [M+1]$^+$ |
| NMR (CDCl$_3$: δ) | 0.50–1.20(6H, m), 1.20–2.50(6H, m), 2.60–3.30(2H, m), 3.35–3.85(3H, m), 3.94(3H, s), 7.00–8.50(6H, m), 9.15–10.10(2H, br) |
| IR (cm$^{-1}$) | 2960, 2860, 2770, 1460, 1250 |
| Elementary analysis (%): as C$_{19}$H$_{27}$NO.HCl | |
| Calcld. | C: 70.90, H: 8.77, N: 4.35 |
| Found | C: 70.55, H: 8.56, N: 4.22 |

EXAMPLE 6

Synthesis of 1-(1-Naphthyl)-2-propylaminopentane Maleic Acid Salt (compound No. 18)

Using the same method as stated in Example 4, starting from 0.5 g (2.0 mmol) of 1-(1-Naphthyl)-2-propylaminopentane which was free base of the compound No. 5, 0.40 g (1.1 mmol) of maleic acid salt of this compound was obtained (55%).

| | |
|---|---|
| m.p. | 137.0–139.0° C. |
| MS | 256 [M + 1]$^+$ (m/z) |
| NMR(CDCl$_3$) | 0.90 (6H, t, J = 8.0 Hz), 1.10–2.20 (6H, m), 2.70–4.00 (5H, m), 6.34 (2H, s), 7.20–8.20 (7H, m), 8.30–10.00 (1H, br) |
| IR | 2950, 1570, 1510, 1380, 1360 (cm$^{-1}$) |

Elementary analysis: as C$_{18}$H$_{25}$N.C$_4$H$_4$O$_4$

| | |
|---|---|
| Calcld. | C: 71.13, H: 7.87, N: 3.77 (%) |
| Found | C: 71.10, H: 7.83, N: 3.63 (%) |

EXAMPLE 7

Synthesis of 1-(Indol-2-yl)-2-propylaminopentane Hydrochloride (compound No. 19)

Using the same method as stated in Examples 1–3, starting from 4.94 g (21.5 mmol) of 1-(indol-2-yl)-2-nitro-1-pentene, 1.43 g (5.1 mmol) of title compound was obtained (24%).

| | |
|---|---|
| m.p. | 61.0–62.0° C. |
| MS | 244 [M]$^+$ (m/z) |
| NMR(CDCl$_3$) | 0.60–1.15 (6H, m), 1.15–1.90 (6H, m), 2.30–3.20 (5H, m), 6.20 (1H, s), 6.80–7.75 (4H, m) |
| IR | 3278, 2948, 2918, 2850, 1449 (cm$^{-1}$) |

Elementary analysis: as C$_{16}$H$_{24}$N$_2$.HCl

| | |
|---|---|
| Calcld. | C: 68.43, H: 8.61, N: 9.97 (%) |
| Found | C: 68.00, H: 8.83, N: 9.77 (%) |

EXAMPLE 8

Synthesis of 1-(Indol-3-yl)-2-propylaminopentane Hydrochloride (compound No. 20)

Using the same method as stated in Examples 1–3, starting from 4.73 g (20.5 mmol) of 1-(indol-3-yl)-2-nitro-1-pentene, 0.46 g (1.6 mnol) of title compound was obtained (8%).

| | |
|---|---|
| m.p. | 149.5–151.0° C. |
| MS | 245 [M + 1]$^+$ (m/z) |
| NMR(CDCl$_3$) | 0.50–1.15 (6H, m), 1.15–2.20 (6H, m), 2.30–4.40 (5H, m), 6.70–7.90 (5H, m), 8.50–9.90 (3H, m) |
| IR | 3225, 2950, 2775, 1450, 740 (cm$^{-1}$) |

Elementary analysis: as C$_{16}$H$_{24}$N$_2$.HCl

| | |
|---|---|
| Calcld. | C: 68.43, H: 8.97, N: 9.97 (%) |
| Found | C: 68.07, H: 8.83, N: 9.71 (%) |

EXAMPLE 9

Synthesis of 1-(Indol-4-yl)-2-propylaminopentane Hydrochloride (compound No. 21)

Using the same method as stated in Examples 1–3, starting from 5.47 g (23.8 mmol) of 1-(indol-4-yl)-2-nitro-1-pentene, 0.23 g (0.8 mmol) of title compound was obtained (3%).

| | |
|---|---|
| m.p. | 151.0–152.0° C. |
| MS | 244 [M]$^+$ (m/z) |
| NMR(CDCl$_3$) | 0.60–1.20 (6H, m), 1.20–2.10 (6H, m), 2.65–3.95 (5H, m), 6.60 (1H, d, J = 3.0 Hz), 6.80–7.60 (4H, m) |
| IR | 3280, 2974, 2802, 1587, 1469, 1334, 1128, 1100, 778, 768 (cm$^{-1}$) |

Elementary analysis: as C$_{16}$H$_{24}$N$_2$.HCl

| | |
|---|---|
| Calcld. | C: 68.43, H: 8.97, N: 9.97 (%) |
| Found | C: 67.95, H: 8.74, N: 9.90 (%) |

EXAMPLE 10

Synthesis of 1-(Indol-6-yl)-2-propylaminopentane Hydrochloride (compound No. 22)

Using the same method as stated in Examples 1–3, starting from 1.74 g (7.7 mmol) of 1-(indol-6-yl)-2-nitro-1-pentene, 0.054 g (0.2 mmol) of title compound was obtained (3%).

| | |
|---|---|
| m.p. | 172.0–173.0° C. |
| MS | 244 [M]$^+$ (m/z) |
| NMR(CDCl$_3$) | 0.68–1.12 (6H, m), 1.12–2.10 (6H, m), 2.65–3.80 (5H, m), 6.42 (1H, d, J = 3.4 Hz), 6.92 (1H, d, J = 8.0 Hz), 7.21 (1H, d, J = 3.4 Hz), 7.36 (1H, s), 7.53 (1H, d, J = 8.0 Hz) |
| IR | 3250, 2967, 2824, 1574, 1458, 1353, 735 (cm$^{-1}$) |

Elementary analysis: as C$_{16}$H$_{24}$N$_2$.HCl

| | |
|---|---|
| Calcld. | C: 68.43, H: 8.97, N: 9.97 (%) |
| Found | C: 68.22, H: 8.82, N: 9.92 (%) |

EXAMPLE 11

Synthesis of 1-(Indol-7-yl)-2-propylaminopentane (compound No. 23)

Using the same method as stated in Examples 1–3, starting from 7.43 g (32.3 mmol) of 1-(indol-7-yl)-2-nitro-1-pentene, 0.84 g (3.0 mmol) of title compound was obtained (9%).

| | |
|---|---|
| MS | 244 [M]$^+$ (m/z) |
| NMR(CDCl$_3$) | 0.60–1.15 (6H, m), 1.15–2.00 (6H, m), 2.50–3.40 (5H, m), 6.48 (1H, d, J = 3.0 Hz), 6.70–7.30 (3H, m), 7.21 (1H, dd, J = 2.0, 6.0 Hz) |
| IR | 2960, 2934, 2876, 1460, 1432, 1342, 794, 750 (cm$^{-1}$) |

EXAMPLE 12

Synthesis of 1-(5-Chloroindol-3-yl)-2-propylaminopentane Hydrochloride (compound No. 24)

Using the same method as stated in Examples 1–3, starting from 6.91 g (26.1 mmol) of 1-(5-chloroindol-3-yl)-2-nitro-1-pentene, 1.30 g (4.1 mmol) of title compound was obtained (16%).

| | |
|---|---|
| m.p. | 66.0–67.0° C. |
| MS | 279 [M + 1]$^+$ (m/z) |
| NMR(CDCl$_3$) | 0.73–1.20 (6H, m), 1.20–2.20 (6H, m), 2.75–3.70 (5H, m), 6.95–7.95 (4H, m) |
| IR | 3226, 2962, 2870, 2795, 1579, 1458, 1099, 885, 800 (cm$^{-1}$) |

Elementary analysis: as $C_{16}H_{23}N_2Cl \cdot HCl$

| | | |
|---|---|---|
| Calcld. | C: 60.95, H: 7.67, N: 8.89 (%) | |
| Found | C: 60.11, H: 7.48, N: 8.77 (%) | |

EXAMPLE 13

Synthesis of 1-(Benzofuran-2-yl)-2-propylaminopentane Hydrochloride (compound No. 25)

Using the same method as stated in Examples 1–3, starting from 7.54 g (98.6 mmol) of 1-(benzofuran-2-yl)-2-nitro-1-pentene, 1.51 g (5.4 mmol) of title compound was obtained (5%).

| | |
|---|---|
| m.p. | 135.0–136.0° C. |
| MS | 264 [M + 1]$^+$ (m/z) |
| NMR(CDCl$_3$) | 0.70–1.20 (6H, m), 0.70–2.40 (6H, m), 2.60–3.90 (5H, m), 6.67 (1H, s), 7.00–7.70 (4H, m), 9.10–10.20 (2H, br) |
| IR | 2954, 2868, 2790, 2736, 2692, 1600, 1587, 1454, 771, 759 (cm$^{-1}$) |

Elementary analysis: as $C_{16}H_{23}NO \cdot HCl$

| | | |
|---|---|---|
| Calcld. | C: 68.19, H: 8.58, N: 4.97 (%) | |
| Found | C: 67.94, H: 8.48, N: 5.16 (%) | |

EXAMPLE 14

Synthesis of 1-(1,3-Benzodioxol-5-yl)-2-aminopentane Hydrochloride (compound No. 26)

Using the same method as stated in Example 1, starting from 10.56 g (44.9 mmol) of 1-(1,3-benzodioxol-5-yl)-2-nitro-1-pentene, 7.12 g (34.4 mmol) of title compound was obtained (77%).

| | |
|---|---|
| m.p. | 199.0–201.0° C. |
| MS | 207 [M]$^+$ (m/z) |
| NMR(CDCl$_3$) | 0.60–1.95 (6H, m), 2.70–3.65 (5H, m), 5.93 (2H, s), 6.77 (3H, s) |
| IR | 3410, 2960, 2925, 2760, 1595, 1495, 1485, 1440, 1248, 1195, 1040, 928 (cm$^{-1}$) |

Elementary analysis: as $C_{12}H_{17}NO_2 \cdot HCl$

| | | |
|---|---|---|
| Calcld. | C: 59.13, H: 7.03, N: 5.75 (%) | |
| Found | C: 59.28, H: 7.32, N: 5.80 (%) | |

EXAMPLE 15

Synthesis of 1-(1,3-Benzodioxol-5-yl)-2-propylaminopentane Hydrochloride (compound No. 27)

Using the same method as stated in Examples 2 and 3, starting from 7.12 g (34.4 mmol) of 1-(1,3-benzodioxol-5-yl)-2-aminopentane obtained by Example 14, 4.41 g (15.4 mmol) of title compound was obtained (45%).

| | |
|---|---|
| m.p. | 139.5–141.5° C. |
| MS | 250 [M + 1]$^+$ (m/z) |
| NMR(CDCl$_3$) | 0.97 (6H, t, J = 7.0 Hz), 1.20–2.50 (6H, m), 2.55–3.75 (5H, m), 5.93 (2H, s), 6.75 (3H, m), 9.05–10.05 (2H, br) |
| IR | 2950, 2860, 2760, 1485, 1440, 1240, 1030 (cm$^{-1}$) |

Elementary analysis: as $C_{15}H_{23}NO_2 \cdot HCl$

| | | |
|---|---|---|
| Calcld. | C: 63.04, H: 8.46, N: 4.90 (%) | |
| Found | C: 62.96, H: 8.26, N: 4.88 (%) | |

EXAMPLE 16

Synthesis of 1-(1,3-Benzodioxol-4-yl)-2-propylaminopentane Hydrochloride (compound No. 28)

Using the same method as stated in Examples 1–3, starting from 10.84 g (46.3 mmol) of 1-(1,3-benzodioxol-4-yl)-2-nitro-1-pentene, 1.43 g (5.0 mmol) of title compound was obtained (11%).

| | |
|---|---|
| m.p. | 103.5–105.0° C. |
| MS | 250 [M + 1]$^+$ (m/z) |
| NMR(CDCl$_3$) | 0.97 (6H, t, J = 7.0 Hz), 1.20–2.40 (6H, m), 2.60–3.70 (5H, m), 5.95 (2H, s), 6.78 (3H, s), 9.00–10.00 (2H, br) |
| IR | 2986, 2882, 2820, 2800, 2748, 1453, 1246, 1054 (cm$^{-1}$) |

Elementary analysis: as $C_{15}H_{23}NO_2 \cdot HCl$

| | | |
|---|---|---|
| Calcld. | C: 63.04, H: 8.46, N: 4.90 (%) | |
| Found | C: 62.73, H: 8.24, N: 4.80 (%) | |

EXAMPLE 17

Synthesis of 1-(1,3-Benzodioxol-5-yl)-2-butylaminopentane Hydrochloride (compound No. 29)

A mixture of 2.0 g (9.7 mmol) of 1-(1,3-benzdioxol-5-yl)pentan-2-one, 0.71 g (9.7 mmol) of n-butylamine, 2.88 g (13.6 mmol) of sodium triacetoxyborohydride and 0.58 g (9.7 mmol) of acetic acid were stirred in 1,2-dichloroethane (34 ml) under argon gas for four days at room temperature. Thereafter, the mixture was alkalized with 1 N sodium hydroxide. Water (50 ml) was added to the mixture and was extracted three times with ether (70 ml). The obtained organic phase was washed with saturated sodium chloride solution and dried over anhydrous sodium sulfate, concentrated and purified by column chromatography. Chloroform was used for eluting solvent. 1-(1,3-Benzodioxol-5-yl)-2-butylaminopentane was obtained as light yellow oil.

Using the same method as stated in Example 1, 1-(1,3-Benzodioxol-5-yl)-2-butylaminopentane was converted to hydrochloride and 1.42 g (4.7 mmol) of title compound was obtained (48%).

| | |
|---|---|
| m.p. | 113.5–115.0° C. |
| MS | 264 [M + 1]+ (m/z) |
| NMR(CDCl$_3$) | 0.69–1.14 (6H, m), 1.15–2.29 (8H, m), 2.61–3.65 (5H, m), 5.94 (2H, s), 6.77 (3H, s), 9.10–10.10 (2H, br) |
| IR | 2952, 2932, 2866, 2790, 2744, 1488, 1449, 1249, 1039 (cm$^{-1}$) |

Elementary analysis: as $C_{16}H_{25}NO_2 \cdot HCl$

| | |
|---|---|
| Calcld. | C: 64.09, H: 8.74, N: 4.67 (%) |
| Found | C: 64.01, H: 8.56, N: 4.64 (%) |

EXAMPLE 18

Using the same method as stated in Example 17, 1-(1,3-benzodioxol-5-yl)pentan-2-one was reacted with alkylamine. The hydrochloride of the corresponding ethylamine derivatives were obtained; compounds No. 30–32 shown in Table 4, and the physicochemical data of the above compounds No. 30-32 were shown in Table 5.

TABLE 4

Compounds No. 30–32

| Compounds No. | A ring | R$^1$ | R$^2$ | R$^3$ | Yield (%) |
|---|---|---|---|---|---|
| 30 | 1,3-Benzodioxol-5-yl | H | —CH$_2$CH$_2$CH$_3$ | —CH(CH$_3$)CH$_2$CH$_3$ | 72 |
| 31 | 1,3-Benzodioxol-5-yl | H | —CH$_2$CH$_2$CH$_3$ | —CH(CH$_2$CH$_3$)$_2$ | 71 |
| 32 | 1,3-Benzodioxol-5-yl | H | —CH$_2$CH$_2$CH$_3$ | —CH$_2$CH$_2$CH$_2$CH$_2$CH$_3$ | 51 |

TABLE 5

Physicochemical properties of compounds No. 30–32

Compound No. 30
| | |
|---|---|
| m.p. (° C.) | 166.0–167.0 |
| MS (m/z) | 264 [M+1]+ |
| NMR (CDCl$_3$: δ) | 0.60–1.20(6H, m), 1.20–2.40(9H, m), 2.50–3.70(4H, m), 5.95(2H, s), 6.79(3H, s), 8.70–9.90(2H, br) |
| IR (cm$^{-1}$) | 2950, 2872, 2810, 2772, 2688, 1500, 1450, 1255, 1039, 927 |
| Elementary analysis (%): as $C_{16}H_{25}NO_2 \cdot HCl$ | |
| Calcld. | C: 64.09, H: 8.74, N: 4.67 |
| Found | C: 64.25, H: 8.54, N: 4.46 |

Compound No. 31
| | |
|---|---|
| m.p. (° C.) | 176.0–177.0 |
| MS (m/z) | 278 [M+1]+ |
| NMR (CDCl$_3$: δ) | 1.03(9H, t, J=8.0Hz), 1.20–2.20(8H, m), 2.40–3.30(4H, m), 5.96(2H, s), 6.79(3H, s), 8.60–9.80(2H, br) |
| IR (cm$^{-1}$) | 2972, 2860, 2748, 2676, 1582, 1496, 1445, 1252, 1136, 922 |
| Elementary analysis (%): as $C_{17}H_{27}NO_2 \cdot HCl$ | |
| Calcld. | C: 65.05, H: 8.99, N: 4.46 |
| Found | C: 64.60, H: 8.83, N: 4.56 |

Compound No. 32
| | |
|---|---|
| m.p. (° C.) | 87.0–88.0 |
| MS (m/z) | 278 [M+1]+ |
| NMR (CDCl$_3$: δ) | 0.70–1.10(6H, m), 1.15–2.30(10H, m), 2.60–3.70(5H, m), 5.97(2H, s), 6.79(3H, s), 9.20–9.90(2H, br) |
| IR (cm$^{-1}$) | 2964, 2935, 2870, 2772, 2720, 1504, 1470, 1449, 1255, 1043, 937 |
| Elementary analysis (%): as $C_{17}H_{27}NO_2 \cdot HCl$ | |
| Calcld. | C: 65.05, H: 8.99, N: 4.46 |
| Found | C: 64.66, H: 8.80, N: 4.52 |

EXAMPLE 19

Synthesis of 1-(1,3-Benzodioxol-5-yl)-2-p-toluidinopentane Hydrochloride (compound No. 33)

Using the same method as stated in Example 17, starting from 2.0 g (9.7 mmol) of 1-(1,3-benzodioxol-5-yl)pentan-2-one, 2.49 g (7.5 mmol) of title was obtained (77%).

| | |
|---|---|
| m.p. | 134.5–136.0° C. |
| MS | 297 [M]+ (m/z) |
| NMR(CDCl$_3$) | 0.50–0.96 (3H, m), 0.98–1.92 (4H, m), 2.33 (3H, s), 2.55–3.80 (3H, m), 5.91 (2H, s), 6.35–6.88 (3H, m), 7.17 (2H, d, J = 8.0 Hz), 7.59 (2H, d, J = 8.0 Hz) |
| IR | 2964, 2928, 2740, 2664, 2468, 1506, 1489, 1446, 1250, 1042 (cm$^{-1}$) |

Elementary analysis: as $C_{19}H_{23}NO_2 \cdot HCl$

| | |
|---|---|
| Calcld. | C: 68.35, H: 7.25, N: 4.20 (%) |
| Found | C: 68.42, H: 7.28, N: 4.16 (%) |

EXAMPLE 20

Synthesis of 1-(1,3-Benzodixol-5-yl)-2-benzylaminopentane Hydrochloride (compound No. 34)

Using the same method as stated in Example 17, starting from 2.0 g (9.7 mmol) of 1-(1,3-benzodixol-5-yl)pentan-2-one, 1.58 g (4.7 mmol) of title compound was obtained (48%).

| | |
|---|---|
| m.p. | 136.0–137.0° C. |
| MS | 298 [M + 1]+ (m/z) |
| NMR(CDCl$_3$) | 0.60–1.05 (3H, m), 1.15–2.00 (4H, m), 2.65–3.60 (3H, m), 3.80–4.40 (2H, br), 5.93 (2H, s), 6.50–6.90 (3H, m), 7.25–7.80 (5H, m), 9.40–10.20 (2H, br) |
| IR | 3442, 2958, 2816, 2720, 1554, 1486, 1455, 1260, 1032, 735 (cm$^{-1}$) |

Elementary analysis: as $C_{19}H_{23}NO_2 \cdot HCl$

| | |
|---|---|
| Calcld. | C: 68.35, H: 7.25, N: 4.20 (%) |
| Found | C: 68.37, H: 7.11, N: 4.15 (%) |

EXAMPLE 21

Synthesis of 1-(1,4-Benzodioxan-6-yl)-2-propylaminopentane Hydrochloride (compound No. 35)

Using the same method as stated in Examples 1–3, starting from 6.02 g (24.2 mmol) of 1-(1,4-benzodioxan-6-yl)-2-nitro-1-pentene, 1.25 g (4.2 mmol) of title compound was obtained (17%).

| | |
|---|---|
| m.p. | 146.0–147.5° C. |
| MS | 264 [M + 1]$^+$ (m/z) |
| NMR(CDCl$_3$) | 0.97 (6H, t, J = 7.0 Hz), 1.30–2.30 (6H, m), 2.50–3.60 (5H, m), 4.24 (4H, s), 6.79 (3H, s), 8.80–10.20 (2H, br) |
| IR | 2948, 2930, 2858, 2774, 2736, 1578, 1497, 1294, 1281, 1253, 1060 (cm$^{-1}$) |

Elementary analysis: as $C_{16}H_{25}NO_2 \cdot HCl$

| | |
|---|---|
| Calcld. | C: 64.09, H: 8.74, N: 4.67 (%) |
| Found | C: 63.94, H: 8.54, N: 4.52 (%) |

EXAMPLE 22

Synthesis of 1-(2,3-Dihydrobenzofuran-5-yl)-2-propylaminopentane Hydrochloride (compound No. 36)

Using the same method as stated in Examples 1–3, starting from 6.95 g (29.8 mmol) of 1-(2,3-dihydrobenzofuran-5-yl)-2-nitro-1-pentene, 0.83 g (2.9 mmol) of title compound was obtained (10%).

| | |
|---|---|
| m.p. | 138.5–140.0° C. |
| MS | 248 [M + 1]$^+$ (m/z) |
| NMR(CDCl$_3$) | 0.96 (6H, t, J = 7.0 Hz), 1.20–2.40 (6H, m), 2.50–3.65 (7H, m), 4.53 (2H, t, J = 9.0 Hz), 6.55–7.35 (3H, m), 8.95–10.00 (2H, br) |
| IR | 3410, 2960, 2865, 2780, 2740, 2520, 2420, 1580, 1485, 1460, 1240, 975, 945 (cm$^{-1}$) |

Elementary analysis: as $C_{16}H_{25}NO \cdot HCl$

| | |
|---|---|
| Calcld. | C: 67.71, H: 9.23, N: 4.93 (%) |
| Found | C: 67.72, H: 9.06, N: 4.92 (%) |

EXAMPLE 23

Synthesis of 1-(Indan-5-yl)-2-propylaminopentane Hydrochloride (compound No. 37)

Using the same method as stated in Examples 1–3, starting from 2.96 g (12.8 mmol) of 1-(indan-5-yl)-2-nitro-1-pentene, 0.28 g (1.0 mmol) of title compound was obtained (8%).

| | |
|---|---|
| m.p. | 153.5–155.0° C. |
| MS | 246 [M + 1]$^+$ (m/z) |
| NMR(CDCl$_3$) | 0.65–1.20 (6H, m), 1.35–2.50 (8H, m), 2.50–3.85 (9H, m), 6.80–7.40 (3H, m), 9.00–10.00 (2H, br) |
| IR | 3420, 2970, 2865, 2825, 2730, 2510, 2415, 1575, 1492, 1452, 810 (cm$^{-1}$) |

Elementary analysis: as $C_{17}H_{27}N \cdot HCl$

| | |
|---|---|
| Calcld. | C: 72.44 H: 10.01 N: 4.97 (%) |
| Found | C: 71.88 H: 9.68 N: 5.07 (%) |

EXAMPLE 24

Synthesis of 1-(2-Benzothienyl)-2-propylaminopentane Hydrochloride (compound No. 38)

Using the same method as stated in Examples 1–3, starting from 11.24 g (45.5 mmol) of 1-(2-benzothienyl)-2-nitro-1-pentene, 2.68 g (9.0 mmol) of title compound was obtained (20%).

| | |
|---|---|
| m.p. | 157.0–159.0° C. |
| MS | 262 [M + 1]$^+$ (m/z) |
| NMR(CDCl$_3$) | 0.65–1.20 (6H, m), 1.20–2.40 (6H, m), 2.50–4.00 (5H, m), 6.95–7.50 (3H, m), 7.50–8.00 (2H, m), 9.20–10.10 (2H, br) |
| IR | 3472, 2960, 2866, 2794, 2740, 2678, 2508, 2418, 1603, 1591, 1455, 1435, 1120, 839, 773, 762, 732 (cm$^{-1}$) |

Elementary analysis: as $C_{16}H_{23}NS \cdot HCl$

| | |
|---|---|
| Calcld. | C: 64.51, H: 8.12, N: 4.70 (%) |
| Found | C: 64.03, H: 7.99, N: 4.61 (%) |

EXAMPLE 25

Synthesis of 1-(3-Benzothienyl)-2-propylaminopentane Hydrochloride (compound No. 39)

Using the same method as stated in Examples 1–3, starting from 8.86 g (35.8 mmol) of 1-(3-benzothienyl)-2-nitro-1-pentene, 0.90 g (3.0 mmol) of title compound was obtained (8%).

| | |
|---|---|
| m.p. | 117.0–119.0° C. |
| MS | 262 [M + 1]$^+$ (m/z) |
| NMR(CDCl$_3$) | 0.35–1.10 (6H, m), 1.10–2.40 (6H, m), 2.40–4.30 (5H, m), 6.70–7.60 (3H, m), 7.60–8.15 (2H, m), 9.10–10.15 (2H, br) |
| IR | 3440, 2964, 2930, 2860, 2784, 2738, 1588, 1579, 1452, 1424, 577, 561, 530 (cm$^{-1}$) |

Elementary analysis: as $C_{16}H_{23}NS\ Cl$

| | |
|---|---|
| Calcld. | C: 64.51, H: 8.12, N: 4.70 (%) |
| Found | C: 64.73, H: 8.01, N: 4.80 (%) |

The results of pharmacological experiments are shown as follows.

EXAMPLE 26

Measurement of Bioenic Amines Released from the Brain Stem of Rat by Electrostimulation The method described in Life Sci., 58, 2101–2114 (1996) was used. Male rats weighing 280–350 g were stunned by a blow on the back of their head, the brain stem (average weight about 800 mg) was excised and soaked in oxygenated (95% $O_2$ and 5% $CO_2$) Krebs solution at 37° C. for 30 min, thereafter 20 μl of one of the $^3$H-noradrenaline (1-[7, 8-$^3$H]-noradrenaline; specific activity: 30–50 Ci/mmol; Amersham) was given to the preparation and 45 min were allotted for uptake. The composition of the Krebs solution was as follows in mmol: $Na^+$ 137.4; $K^+$ 5.9; $Ca^{2+}$ 2.5; $Mg^{2+}$ 1.2; $Cl^-$ 120.2; $H_2PO_4^-$ 1.2; $HCO_3^-$ 25.0; $SO_4^{2-}$ 1.2 and glucose 11.5; 0.3 ascorbic acid and 0.03 EDTA-2 Na. During the period of the uptake of labeled transmitter, pargyline (12 mmol) was present in the Krebs solution for blocking MAO activity. After uptake of $^3$H-oradrenaline, the brain stem was fixed in organ bath containing 5 ml of Krebs solution (37° C.). The brain was then washed with a speed of 8 ml/min with oxygen saturated Krebs solution containing 0.03 mmol/l of cocaine. At the end of 100 min, perfusion was decreased to 4 ml/min and the Krebs solution was modified to contain also 0.05 mmol/l of corticosterone. The experiment was carried out in the presence of cocaine and corticosterone. In this condition, 86% of $^3$H-noradrenaline is not metabolized and is not taken up either neuronally or extra-neuronally. Fractionation of perfusate was carried out every 3 min. The amount of $^3$H-noradrenaline released during each 3 min period was determined by 1 ml of the perfusate dissolved in 5 ml of Aquasafe 300 PLUS (Zinsser) and by scintillation counting (Beckman LS-9000). Using the same method as stated in this experiment, the amount of $^3$H-serotonin was determined. The brain stem was stimulated with rectangular pulses (3 Hz, 1 ms, 60 V) for 3 min. At the beginning of the experiment, the three resting periods of fraction were proceeded before the first stimulation. Thereafter seven resting periods of fraction were allotted between stimulations. The compounds of this invention were solved in perfusate and the solutions of 0.5. 1, 2.5 and 5 μg/ml were prepared. The perfusates including the compounds of this invention were perfused for 3 min before stimulants.

Figure 1:
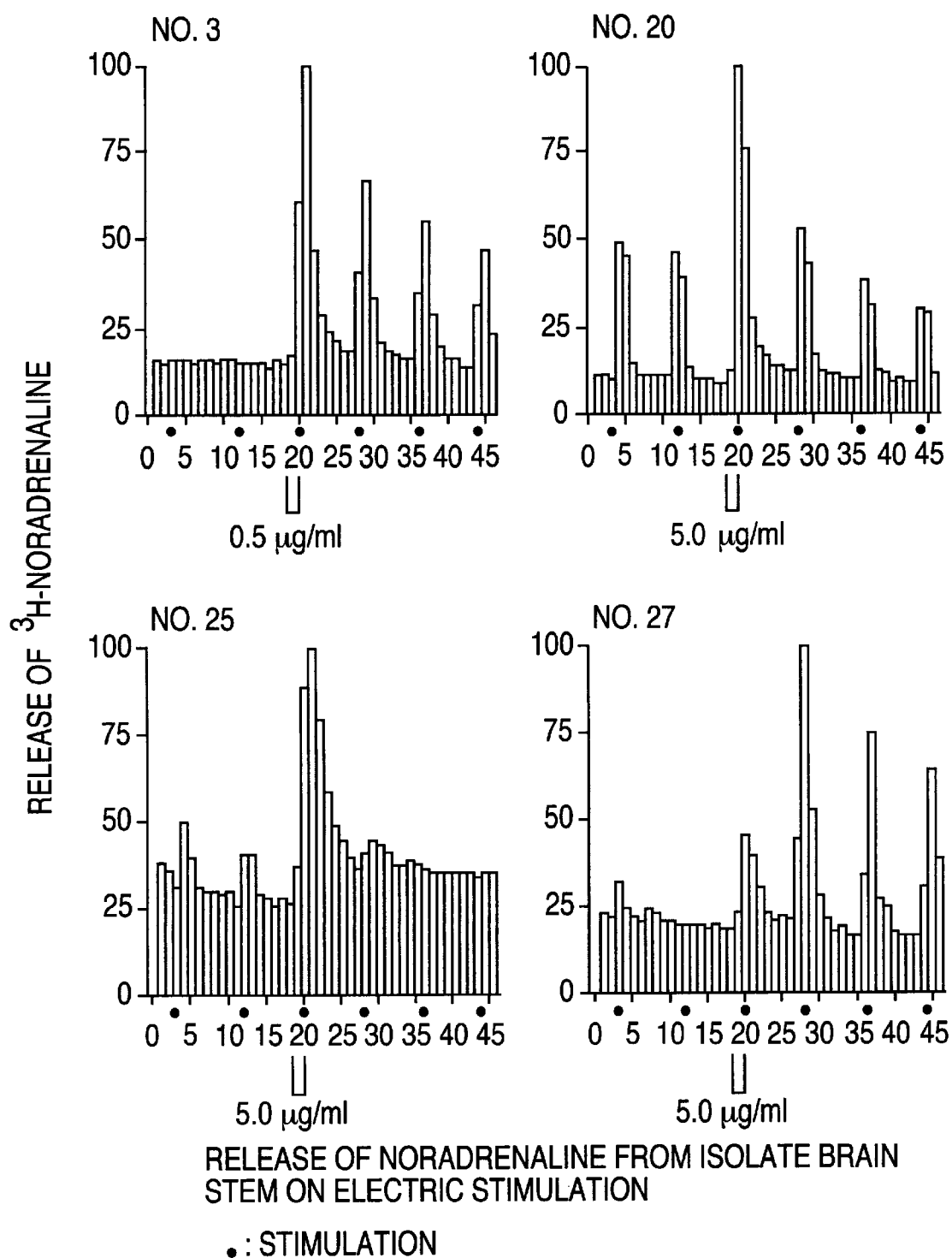
FIG. 1: Noradrenaline releasing effects of compounds Nos. 3, 20, 25 and 27 from electro stimulated isolated brain stem of rats.

The results were shown in FIG. 1 and FIG. 2. As shown therein, the compounds of this invention have been confirmed to enhance releasing noradrenaline and serotonin and to increase the exocytosis, when electrostimulation were given to the nerve cells.

EXAMPLE 27

The Effects on Conditioned Avoidance Task in the Shuttle Box

The method described in Life Sci., 58, 817–827 (1996) was used. The effects on conditioned avoidance reflex (CARs) was analyzed in the shuttle box using male and female rats (weighing 200–220 g) whose leaning abilities were reduced by treatment of tetrabenazine. The instrument was constructed, according to the device described in Psychopharmacologia 10, 1–5 (1966) by the Research Institute for Electrical Industry (Budapest, Hungary). The male and female rats (weighing 200–220 g) were trained to cross the berrier under the influence of a conditioned stimulus (CS) (light flash and buzzer sounds). If they failed to do so, they were punished a footshock (1 mA), i.e. an unconditioned stimulus (US). If the rats failed to respond within 5 sec to US, it was noted as an escape failure (EF). And the performance which was not related to this condition was noted as an intersignal reaction (IR). The rats were trained with 100 trials per day for 5 days. One trial consisted of 15 sec intertrial interval. The saline solution of tetrabenazine was administered at a dose of 1 mg/kg subcutaneously before one hour prior to the test and then the solution of the compounds of this invention were administered at the doses of 1, 2, 2.5 and 5 mg/kg subcutaneously with the simultaneous administration of tetrabenazine. The nmbers of CARs, EFs and IRs were automatically counted and evaluated by multi-way analysis of variance (ANOVA).

The statistical significant differences in the results were shown in Table 6 and the characteristic results were shown in FIGS. 3–6. Thus, the compounds of this invention have been found to improve significantly the reduced learning function of the rats induced by the administration of tetrabenazine and to improve their depression and cognition. As EFs were decreased significantly, it is considered that these compounds may improve the freezing induced by depression or Parkinson's disease. Furthermore, differently from 1-phenyl-2-propyl-aminopentane (PPAP) and the like which are representative compounds disclosed in WO 88/2254, these compounds did not increase significantly the number of IRs which shows the abnormal behavior (excitation).

TABLE 6

The effects of the rats reduced learning ability on conditioned avoidance task (Example 25)

| Compound No. | Dose (mg/kg) | Condition Avoidance Reflex (CARs) | Intersignal Reactions (IRs) | Escape Failures (EFs) |
|---|---|---|---|---|
| PPAP | 5 | **** ↑ | **** ↑ | **** ↓ |
| No. 3 | 1 | **** ↑ | NS | **** ↓ |
| | 2 | **** ↑ | NS | **** ↓ |
| | 2.5 | **** ↑ | * ↓ | *** ↓ |
| | 5 | **** ↑ | NS | **** ↓ |
| | 1 | *** ↑ | NS | **** ↓ |
| No. 6 | 1 | **** ↑ | NS | * ↓ |
| | 5 | **** ↑ | NS | * ↓ |
| No. 15 | 5 | * ↑ | NS | NS |
| No. 20 | 1 | * ↑ | NS | NS |
| | 2.5 | **** ↑ | NS | **** ↓ |
| | 5 | **** ↑ | * ↓ | * ↓ |
| | 1 | **** ↑ | NS | **** ↓ |
| No. 21 | 0.5 | ** ↑ | NS | NS |
| | 1 | **** ↑ | NS | NS |
| No. 22 | 0.5 | * ↑ | NS | NS |
| | 1 | *** ↑ | NS | NS |
| | 5 | **** ↑ | NS | * ↓ |
| No. 25 | 1 | **** ↑ | NS | * ↓ |
| | 5 | **** ↑ | * ↑ | * ↓ |
| No. 27 | 1 | *** ↑ | NS | *** ↓ |
| No. 28 | 1 | * ↑ | NS | NS |
| | 2.5 | **** ↑ | NS | **** ↓ |
| | 5 | **** ↑ | NS | *** ↓ |

TABLE 6-continued

The effects of the rats reduced learning ability
on conditioned avoidance task (Example 25)

| Compound No. | Dose (mg/kg) | Condition Avoidance Reflex (CARs) | Intersignal Reactions (IRs) | Escape Failures (EFs) |
|---|---|---|---|---|
| No. 29 | 2.5 | * ↑ | NS | NS |
|  | 5 | *** ↑ | *** ↓ | NS |
| No. 30 | 5 | **** ↑ | * ↓ | NS |
| No. 33 | 5 | * ↑ | * ↓ | NS |
| No. 37 | 5 | * ↑ | NS | NS |
| No. 38 | 1 | NS | NS | **** ↓ |
|  | 2.5 | **** ↑ | * ↑ | **** ↓ |
| No. 39 | 1 | NS | NS | *** ↓ |
|  | 2.5 | **** ↑ | NS | **** ↓ |

*: $P < 0.05$, : $P < 0.02$, *: $P < 0.01$, ****: $P < 0.001$, NS: No Significancy
↑: increase, ↓: decrease

EXAMPLE 28

Measurement of Transmembrane Ionic Currents in the Sino-auricular Fibers of the Frog Heart A modified version of the voltage clamping method on a double sucrose gap arrangement which was described in Life Sci., 58, 2101–2114 (1996) was used. A fiber about 100 μm diameter, and 3 to 4 mm length was prepared under a binocular microscope from the sino-auricular region of the heart of Rana esculent frogs. The fiber was mounted in a special organ dish in a cooled environment (18±0.5° C.) and five compartments were formed by placing four vaseline barriers of 0.1 mm width along the length of the fiber. The central compartment was perfused with the test solution, which is the solution of the compounds of this invention dissolved at the concentrations of 0.5, 1, 2, 4 and 8 μg/ml in $Na^+$-free Ringer (chorine chloride Ringer), and two lateral compartments were depolarized by isotonic KCl solution. The remaining two compartment, adjacent to the central one, were perfused with isotonic sucrose solution to isolate the central comparment, electrically from the lateral compartment. Command potential was forced on the membrane via non-polarizing $Ug/Hg_2Cl_2$ electrodes to the central and the two lateral compartments. An integrator type feed-back amplifier kept membrane potential constant and measured compensatory current to equivalent of membrane current. Slow inward calcium current was measured by perfusion of the test compartment with $Na^+$-free Ringer (choline chloride Ringer).

The result was shown in FIG. 7. It was confirmed that the compounds of this invention increased slow inward calcium current and have the amplifying effect of the membrane potential dependent exocytosis. Thus, the compounds of this invention have been found to show CAE effect.

EXAMPLE 29

Measurement of Biogenic Amines Released from Brain Tissue

The method described in Life Sci., 56, 611–620 (1995) was used. After Wistar rats were decapitated, appropriate brain samples, which were striatun, substantia nigra, tuberculum olfactorium, locus coeruleus and raphe, were removed quickly and soaked in oxygenated (95% $O_2$ and 5% $CO_2$) Krebs solution at 37° C. The composition of Krebs solution was as follows in mol/l: NaCl 111, KCl 4.7, $CaCl_2$ 2.5, $MgSO_4$ 1.64, $NaHCO_3$ 25, $KH_2PO_4$ 1.2, glucose 11, 50 mg/l ascorbic add and 20 mg/l EDTA-2 Na. The preparations, soaked in one organ bath, were as follows: 1) four pieces of striatum (each halved), 2) four pieces of substantia nigra, 3) four pieces of tuberculum olfactorium; 4) eight pieces of locus coeruleus; 5) eight pieces of raphe. After incubation of the appropriate tissue for 20 min, the Krebs solution was replaced, the tissue soaked for 20 min in Krebs solution dissolving the compounds of this invention and the amount of biogenic amine released during this period of time was estimate. The compounds of this invention and PPAP, control compound, were dissolved in saline and were administered subcutaneously before 30 min to removing brain sample. For measuring noradrenaline and dopamine, samples were purified on 60 mg alumina containing micro columns (BDH Chemicals Ltd.) according to the method described in J. Pharmacol. Exp. Ther., 138, 360–372 (1962) For measuring serotonin, samples were purified on 15 mg Sephadex G-10 micro columns (Pharmacia). Dopamine, noradrenaline and serotonin were determined by high performance liquid chromatography (Waters 746 data module) with electrochemical detection (Waters 460 electrochemical detector). Waters Resolve 5μ Spherical $C_{18}$ 3.9×150 mm column was used as separating column and triethylamine-phosphate buffer (pH 5.2), containing 200 mg/l octane sulfonate sodium and 18 mg/l EDTA-2 Na with 6% acetonitrile, was used as mobile phase. The release amount of appropriate amine was noted as nmol/g tissue released for 20 min. deference of means tested by Student's t-test and significant level was set at $P<.05$.

The result was shown in Table 7. The compounds of this invention significantly increased the dopamine release on striatum, substantia nigra and tuberculum olfactorium. The compounds of this invention significantly also increased noradrenaline release on locus coeruleus and serotonin release on raphe.

TABLE 7

Release of biogenic amines from brain regions (nmol/g tissue, for 20 min)

| Treatment | Dose (mg/kg) | Dopamine | | |
|---|---|---|---|---|
|  |  | striatum | Substantia nigra | Tuberculum olfactorium |
| (±)-PPAP | 0 | 2.9 ± 0.12 | 3.4 ± 0.08 | 2.8 ± 0.07 |
|  | 0.25 | 3.5 ± 0.19* | 4.0 ± 0.24** | 3.7 ± 0.10**** |
|  | 1.00 | 3.6 ± 0.19** | 4.0 ± 0.21** | 3.2 ± 0.21 |
| No. 3 | 0 | 2.9 ± 0.20 | 3.4 ± 0.08 | 2.8 ± 0.07 |
|  | 1.00 | 3.9 ± 0.12**** | 4.5 ± 0.07**** | 5.2 ± 0.12**** |
|  | 0 | 3.4 ± 0.06 | 3.8 ± 0.08 | 3.5 ± 0.09 |
|  | 0.25 | 3.4 ± 0.03 | 4.9 ± 0.07**** | 4.3 ± 0.09**** |
|  | 1.00 | 3.2 ± 0.06 | 8.2 ± 0.46**** | 5.0 ± 0.16**** |
|  | 5.00 | 3.8 ± 0.04**** | 9.0 ± 0.50**** | 5.1 ± 0.39**** |
| No. 5 | 0 | 3.0 ± 0.03 | 3.1 ± 0.06 | 3.8 ± 0.06 |
|  | 0.25 | 4.3 ± 0.14**** | 5.6 ± 0.18**** | 6.0 ± 0.16**** |
|  | 1.00 | 3.2 ± 0.14 | 4.4 ± 0.16**** | 4.6 ± 0.13*** |
| No. 6 | 0 | 3.2 ± 0.11 | 4.5 ± 0.08 | 3.5 ± 0.10 |
|  | 1.00 | 3.6 ± 0.12* | 6.7 ± 0.26**** | 5.3 ± 0.19**** |
| No. 10 | 0 | 3.2 ± 0.11 | 4.5 ± 0.08 | 3.5 ± 0.10 |
|  | 1.00 | 3.3 ± 0.22 | 6.2 ± 0.31*** | 5.6 ± 0.35*** |
| No. 20 | 0 | 3.8 ± 0.15 | 6.7 ± 0.31 | 4.6 ± 0.15 |
|  | 0.005 | 5.8 ± 0.11**** | 8.7 ± 0.13* | 7.0 ± 0.25**** |
|  | 0.01 | 6.5 ± 0.12**** | 10.3 ± 0.23**** | 8.0 ± 0.17**** |
|  | 0 | 3.2 ± 0.11 | 4.5 ± 0.08 | 3.5 ± 0.01 |
|  | 0.25 | 3.2 ± 0.05 | 5.2 ± 0.26* | 3.5 ± 0.21 |
|  | 1.00 | 4.2 ± 0.15*** | 6.7 ± 0.19**** | 4.3 ± 0.07**** |
|  | 5.00 | 4.7 ± 0.13**** | 5.7 ± 0.18**** | 4.8 ± 0.09**** |
|  | 0 | 3.2 ± 0.04 | 5.6 ± 0.27 | 3.7 ± 0.16 |

TABLE 7-continued

Release of biogenic amines from brain regions (nmol/g tissue, for 20 min)

|  | 0.01 | 5.8 ± 0.18**** | 10.0 ± 0.14**** | 5.5 ± 0.20**** |
|---|---|---|---|---|
|  | 0.05 | 5.6 ± 0.13**** | 7.7 ± 0.15**** | 5.8 ± 0.19**** |
| No. 21 | 0 | 4.2 ± 0.17 | 5.3 ± 0.22 | 5.2 ± 0.25 |
|  | 0.01 | 5.4 ± 0.17*** | 10.0 ± 0.30**** | 7.4 ± 0.15**** |
| No. 22 | 0 | 4.2 ± 0.17 | 5.3 ± 0.22 | 5.2 ± 0.25 |
|  | 0.01 | 6.5 ± 0.06**** | 11.9 ± 0.39**** | 9.7 ± 0.17**** |
| No. 25 | 0 | 4.2 ± 0.17 | 5.3 ± 0.22 | 5.2 ± 0.25 |
|  | 0.01 | 5.3 ± 0.14*** | 6.6 ± 0.04*** | 6.5 ± 0.20*** |
| No. 27 | 0 | 3.2 ± 0.11 | 4.5 ± 0.08 | 3.5 ± 0.10 |
|  | 0.10 | 3.4 ± 0.10 | 7.8 ± 0.44**** | 4.7 ± 0.13**** |
|  | 0.25 | 4.1 ± 0.24** | 9.5 ± 0.32**** | 5.2 ± 0.23**** |
| No. 28 | 0 | 3.2 ± 0.11 | 4.5 ± 0.08 | 3.5 ± 0.10 |
|  | 0.25 | 3.4 ± 0.16 | 6.1 ± 0.35*** | 3.8 ± 0.22 |
|  | 1.00 | 4.0 ± 0.18*** | 5.4 ± 0.27** | 4.6 ± 0.22*** |
|  | 5.00 | 3.1 ± 0.13 | 4.9 ± 0.17 | 3.1 ± 0.14 |
| No. 38 | 0 | 4.2 ± 0.17 | 5.3 ± 0.22 | 5.2 ± 0.25 |
|  | 0.01 | 7.9 ± 0.19**** | 14.0 ± 0.23**** | 11.5 ± 0.14**** |
| No. 39 | 0 | 4.2 ± 0.17 | 5.3 ± 0.22 | 5.2 ± 0.25 |
|  | 0.01 | 7.1 ± 0.15**** | 12.0 ± 0.34*** | 10.9 ± 0.25*** |

| Treatment | Dose (mg/kg) | Noradrenaline Locus coeruleus | Serotonin Raphe |
|---|---|---|---|
| (±)-PPAP | 0 | 3.5 ± 0.18 | 0.425 ± 0.02 |
|  | 0.25 | 3.8 ± 0.30 | 0.416 ± 0.03 |
|  | 1.00 | 4.6 ± 0.15* | 0.741 ± 0.01*** |
| No. 3 | 0 | 3.5 ± 0.18 | 0.425 ± 0.02 |
|  | 1.00 | 2.6 ± 0.10* | 0.312 ± 0.01* |
|  | 0 | 3.6 ± 0.10 | 0.434 ± 0.01 |
|  | 0.25 | 4.4 ± 0.10* | 0.958 ± 0.03**** |
|  | 1.00 | 3.2 ± 0.15 | 0.976 ± 0.06**** |
|  | 5.00 | 2.2 ± 0.11 | 1.215 ± 0.14**** |
| No. 5 | 0 | 3.2 ± 0.15 | 0.406 ± 0.02 |
|  | 0.25 | 3.9 ± 0.25 | 0.425 ± 0.02 |
|  | 1.00 | 4.4 ± 0.50 | 0.571 ± 0.01* |
| No. 6 | 0 | 3.5 ± 0.10 | 0.473 ± 0.02 |
|  | 1.00 | 3.1 ± 0.05 | 0.708 ± 0.07* |
| No. 10 | 0 | 3.5 ± 0.10 | 0.473 ± 0.02 |
|  | 1.00 | 2.9 ± 0.15 | 0.603 ± 0.10* |
| No. 20 | 0 | 3.9 ± 0.30 | 0.400 ± 0.01 |
|  | 0.005 | 5.3 ± 0.30 | 0.492 ± 0.02 |
|  | 0.01 | 4.3 ± 0.10 | 0.961 ± 0.02** |
|  | 0 | 3.0 ± 0.02 | 0.473 ± 0.02 |
|  | 0.25 | 4.3 ± 0.15**** | 0.481 ± 0.05 |
|  | 1.00 | 4.4 ± 0.25* | 0.355 ± 0.05 |
|  | 5.00 | 3.5 ± 0.20 | 0.565 ± 0.01 |
|  | 0 | 3.3 ± 0.05 | 0.541 ± 0.01 |
|  | 0.01 | 2.2 ± 0.15* | 0.938 ± 0.01**** |
|  | 0.05 | 3.2 ± 0.15 | 1.203 ± 0.08** |
| No. 21 | 0 | 4.5 ± 0.25 | 0.428 ± 0.01 |
|  | 0.01 | 4.6 ± 0.40 | 0.354 ± 0.00** |
| No. 22 | 0 | 4.5 ± 0.25 | 0.428 ± 0.01 |
|  | 0.01 | 4.8 ± 0.05 | 0.322 ± 0.01** |
| No. 25 | 0 | 4.5 ± 0.25 | 0.428 ± 0.01 |
|  | 0.01 | 4.3 ± 0.20 | 0.457 ± 0.04** |
| No. 27 | 0 | 3.5 ± 0.10 | 0.473 ± 0.02 |
|  | 0.10 | 3.8 ± 0.15 | 0.399 ± 0.00 |
|  | 0.25 | 3.5 ± 0.20 | 0.414 ± 0.01 |
| No. 28 | 0 | 3.0 ± 0.01 | 0.473 ± 0.02 |
|  | 0.25 | 3.6 ± 0.35 | 1.031 ± 0.03*** |
|  | 1.00 | 3.7 ± 0.10** | 1.017 ± 0.06** |
|  | 5.00 | 3.9 ± 0.10** | 1.436 ± 0.01**** |
| No. 38 | 0 | 4.5 ± 0.25 | 0.428 ± 0.01 |
|  | 0.01 | 3.6 ± 0.05 | 0.375 ± 0.02* |
| No. 39 | 0 | 4.5 ± 0.25 | 0.428 ± 0.01 |
|  | 0.01 | 4.1 ± 0.15 | 0.256 ± 0.01*** |

*: $P < 0.05$, : $P < 0.02$, *: $P < 0.01$, ****: $P < 0.001$, vs. Control (0 mg/kg)

EXAMPLE 30

The Releasing Effect of Monoamines in Synaptosomes of the Rat Brain

Synaptosomes were prepared as follows. Fresh striatum (for determination of dopamine) and fresh forebrain (for determination of noradrenaline and serotonin) were removed from listar rats of 8 weeks old (NIPPON S. L. C.). Ten times volumes of ice-cold 0.35 M sucrose (pH 7.4) were added in the brain tissue and homogenized using glass homogenizer with teflon pestle which was revolted by motors. Thereafter the homogenate was centrifuged at 900×g for 10 min at 4° C. and the supernatant was recentrifuged at 11,500×g for 20 min. The pellet was resuspeded in ice-cold buffer. Final concentration of synaptosomes was prepared to 0.6 mg protein/ml. Protein concentration was determined by method described in Journal of Biological Chemistry, 193, 265–275 (1951) and the bovine serum albumin was used as an authentic standard. The release of monoamine from synaptosomes was determined by the following procedure based on the method described in Journal of Pharmacology and Experimental Therapeutics, 241, 27–33 (1987). The solution of 0.6 mg/ml of synaptosomes was preincubated for 5 min at 35° C. under the oxygenated (95% $O_2$ and 5% $CO_2$) condition. Thereafter 25 nM $^3$H-monoamines were added in synaptosomal solution and the solutions were incubated for 5 min at 35° C. The synaptosomes solutions were then pipetted into chamber and were perfused with continuous 0.7 ml/min of superfusion buffer for 25 min at 35° C. to remove excess labeled compounds. Thereafter $^3$H-monoamines which were released from synaptosomes were collected each 0.25 ml continuously at 2 min intervals for 20 min. The compounds of this invention was continuously added in superfusion buffer from fraction 5 (10 min) as synaptosome was always exposed by the compounds of this invention of which final concentration of this compounds was kept to $10^{-5}$ M. 3.5 ml of the scintillation cocktails (EMULSIFIER SCINTILLATOR PLUS8 [Packard]) were added in the collected superfusion buffer and $^3$H released from synaptosomes was determined with scintillation counter.

The composition of used superfusion buffer was as follows in mol/l; NaCl 115, $CaCl_2$ 2, $MgSO_4$ 1.5, $KH_2PO_4$ 1.5, $NaHCO_3$ 25, D-glucose 10, ethylene glycol bis(aminoetyl-N, N'-tetra acetic acid (EGTA) 0.5 and L-ascorbic acid 0.1 (pH 7.4).

The results were shown in FIGS. 8 and 9. The compounds of this invention not only showed no tyramine-like effect in synaptosomes but also showed antagonism against the effect of tyramine when added at the same time. These actions simply show that the compounds of this invention have no the tyramine-like releasing effects to displace catecholamines from their storage place and/or inhibit those effects. Therefore, the compoundsd of this invention show high selectivity for the CAE effect.

EXAMPLE 31

Effect on the Monoamine Oxidase (MAO)

Human blood added with 3.8% citric acid was centrifuged at 950 rpm for 10 min and platelet rich plasma (PRP) was obtained. The residual blood cell was centrifuged at 3,000 rpm for 10 min and platelet poor plasma (PPP) was obtained. After blood platelets were measured from a part of PRP, PRP and PPP were frozen at −20° C. They were thawed and were sonicated to be dispersed and suspended when MAO activity was measured. The suspension was used as enzyme for MAO activity assay in blood platelets. In addition, almost all of MAO in blood platelets have been known to be B type.

MAO-B activity was determined according to the method described in Biochem. Pharmacol., 14, 1684–1685 (1965). To 62.5 mM of phosphate buffer solution (880 μgl), 120 μl of solutions of selegiline (reference) or the compounds of this invention prepared to each concentration in phosphate buffer were added. The mixture was incubated at 37° C. for 5 min. After 80 μl of PRP or PPP was added to it, the mixture was incubated at 37° C. for 20 min. Thereafter, 120 μl of substrate (0.33 mg/ml kynuramine dihydrobromide) was added thereto. After incubation at 37° C. for 30 min, 800 μl of 10% trichloroacetic acid were added to stop the reaction and the solution was centrifuged at 3,000 rpm for 10 min. To 1 ml of the supernatant, 2 ml of 1 N NaOH was added and fluorescence of the solution was measured at Ex 312 nm and Em 380 nm. PRP was prepared to 250,000 cell/μl as amounts of blood platelets with 62.5 nM phosphate buffer solution and 4-hydroxyquinoline was used as standard for measurement.

The results were shown in Table 8. MAO-B inhibition rate of selegiline as a reference was 98.1% at $10^{-7}$ M. However, the inhibition rates of the compounds of this invention were less more than 50% at $10^{-5}$ M. It shows that the compounds of this invention have no MAO-B inhibitory effect. Therefore, it has been supported that the compounds of this invention have high selectivity for the CAE effects

TABLE 8

Inhibitory effects of the compounds on human platelet MAO-B

| Compounds | Concentration | Inhibition rate of MAO-B (%) |
|---|---|---|
| Selegiline | $10^{-7}$ M | 98.1% |
| Compound No. 5 | $10^{-5}$ M | 17.3% |
| Compound No. 6 | $10^{-5}$ M | 24.5% |
| Compound No. 10 | $10^{-5}$ M | 37.2% |
| Compound No. 20 | $10^{-5}$ M | 6.4% |
| Compound No. 27 | $10^{-5}$ M | 34.0% |
| Compound No. 28 | $10^{-5}$ M | 22.2% |

EXAMPLE 32

The Affinities to Receptors of $\alpha_1$, $\alpha_2$, $D_1$, $D_2$, 5-$HT_1$ and 5-$HT_2$ The solution of receptor was prepared as follows. As soon as rats were decapitated, brain was removed and its weight was measured. Its brain was homogenized in ten times volumes of ice-cold 0.35 M sucrose (pH 7.4) by glass homogenizer with teflon pestle which was revolted by motors. Thereafter, the homogenate was centrifuged at 4° C. at 900×g for 10 min and the supernatant was, furthermore, recentrifuged at 4° C. at 22,000×g for 20 min. The precipitate was suspended by addition of 5 mM phosphate buffer solution (pH 7.4). After the suspension was incubated at 37° C. for 30 min, the suspension was recentrifuged at 4° C. at 22,000×g for 20 min. The precipitate was resuspended by addition of 10 ml of 5 mM phosphate buffer solution (pH 8.0). The precipitate was used as the solution of receptor.

$^3$H-prazocin was used as a ligand. 0.25 nM $^3$H-prazocin in 5 mM phosphate buffer (pH 8.0), the compound of this invention and the solution of receptor were added in tube and the mixture were incubated at 25° C. for 90 min. In addition, the nonvolatile binding was shown by binding value of $^3$H-prazocin under the coexistence with 0.1 μM prazocin. The binding reaction was carried out as follows. After $^3$H-prazocin (binding type: B) bound to receptor using glassfiberfilter (pore size: 0.5 μm, Whatman GF/C.) and free type of prazocin (free type: F) were separated with B/F separator (Brandel, USA), only the binding type of $^3$H-prazocin was collected. The binding type of $^3$H-prazocin absorbed to glass-fiber filter was washed with ice-cold saline solution and was remove to vial. After 10 ml of scintillation cocktail was added in it, the radioactivity was determined. From the binding inhibition rate of $\alpha_1$ receptor and ligand, affinity of the compounds of this invention to $\alpha_1$ receptor was measured.

Using the same method, affinities of the compounds of this invention to receptor of $\alpha_2$, $D_1$, $D_2$, 5-$HT_1$ and 5-$HT_2$ were respectively determined using 0.7 nM $^3$H-rauwolscine, 1.4 nM $^3$H-SCH-23390, 2.0 nM spiperone, 2 nM $^3$H-5-HT and 0.5 nM $^3$H-ketanserin as their respective ligands. Then 1 μM yohimbine, 10 μM (+)-butaclamol, 10 μM haloperidol, 10 μM 5-HT and 1 μM ketanserin which were their displacers.

If affinity of certain compound to a receptor is high, the binding ligand and receptor is inhibited. Generally, if the mole concentration for 50% inhibition of the binding of each ligand and receptor is not less than $10^{-6}$ M, it is considered that its compound do not have the activity enough to show physiological activity. The compounds of this invention need not less than $10^{-6}$ M or $10^{-5}$ M to inhibit the binding to each receptor as shown Table 9. Therefore it was shown that the compounds of this invention do not have the affinity to recptor necessary for exhibiting physiological activity.

TABLE 9

Affinity of the compounds to receptors *

| Compounds | $\alpha_1$ | $\alpha_2$ | $D_1$ | $D_2$ | 5-$HT_1$ | 5-$HT_2$ |
|---|---|---|---|---|---|---|
| Selegiline | >$10^{-5}$ | $2 \times 10^{-6}$ | >$10^{-5}$ | >$10^{-5}$ | >$10^{-5}$ | >$10^{-5}$ |
| Bromocriptine | $10^{-8}$ | $10^{-7}$ | $10^{-5}$ | $10^{-8}$ | $10^{-7}$ | $10^{-6}$ |
| Compound No. 20 | $8 \times 10^{-5}$ | $9 \times 10^{-7}$ | >$10^{-5}$ | >$10^{-5}$ | $7 \times 10^{-6}$ | >$10^{-5}$ |
| Compound No. 21 | >$10^{-5}$ | $7 \times 10^{-7}$ | >$10^{-5}$ | >$10^{-5}$ | >$10^{-5}$ | >$10^{-5}$ |
| Compound No. 25 | >$10^{-5}$ | $10^{-6}$ | >$10^{-5}$ | >$10^{-5}$ | >$10^{-5}$ | $2 \times 10^{-5}$ |

* $MIC_{50}$

The results of safety tests was shown as follows.

EXAMPLE 33

Toxicity Screening Using Primary Cultured Hepatocyte

The hepatocytes was prepared from rat liver by collagenase perfusion method and suspension containing $5 \times 10^5$ cells/ml were prepared. After cultivation for 24 hr, the suspension was exchanged to the William's Medium E (GIBCO BRL) containing 10 or 100 μM of the compounds of this invention. After cultivation for 24 hr, the activity of lactate dehydrogenase (LDH) released in the medium was measured.

The results of LDH release were shown in percent of control (0.5% saline or 0.5% DMSO) in Table 10. On the treatment with 100 μM concentration, the amount of LDH which were released by the compounds of this invention were the same as or less than that by 1-phenyl-2-propylaminopentane (PPAP) which was disclosed in WO 88/2254 to be a promising psychotropic drug. However, in the presence of the 10 μM concentration, only PPAP released LDH significantly.

TABLE 10

Percent control of LDH release from primary cultured hepatocyte in the presence of compounds

| Concentration of Treatment | 100 μM | 10 μM |
| --- | --- | --- |
| PPAP | 151.83 ± 11.08 *** | 126.80 ± 5.45 * |
| Compound No. 5 | 195.47 ± 9.16 ### | 110.63 ± 4.02 |
| Compound No. 14 | 130.81 ± 7.08 ## | 107.84 ± 4.18 |
| Compound No. 19 | 179.88 ± 5.54 # | 82.38 ± 8.34 |
| Compound No. 20 | 185.30 ± 3.45 ## | 92.72 ± 5.31 |
| Compound No. 21 | 129.98 ± 9.68 # | 109.71 ± 4.42 |
| Compound No. 25 | 112.10 ± 36.98 | 90.28 ± 2.85 |
| Compound No. 27 | 113.97 ± 11.19 | 115.35 ± 10.76 |
| Compound No. 28 | 147.58 ± 6.55 ### | 92.98 ± 6.92 |
| Compound No. 29 | 101.47 ± 2.94 | 103.19 ± 6.02 |
| Compound No. 30 | 138.36 ± 4.57 ### | 99.46 ± 5.44 |
| Compound No. 31 | 152.88 ± 4.35 ### | 102.47 ± 0.84 |
| Compound No. 33 | 151.81 ± 5.71 ### | 94.00 ± 4.16 |
| Compound No. 35 | 147.28 ± 5.07 ### | 103.28 ± 10.57 |
| Compound No. 36 | 110.66 ± 6.58 | 101.43 ± 2.24 |
| Compound No. 37 | 193.03 ± 8.51 ### | 83.80 ± 5.65 |

\*: P < 0.05,   \*\*: P < 0.01,   \*\*\*: P < 0.0001 v.s. 0.5% - Saline
\#: P < 0.05,   \#\#: P < 0.01,   \#\#\#: P < 0.0001 v.s. 0.5% - DMSO The column of 10 μM of the compound No. 23 shows the data obtained by treatment of 20 μM.

EXAMPLE 34

Toxicity Test in Mice in the Single Administration

After the compounds of Examples 3, 25, 27 and 28 were administered subcutanously to mice, general symptoms of the mice were observed every day for two weeks. Consequently, all the mice survived to which these compounds were administered at the dose of 50 mg/kg in all case.

What is claimed is:

1. Ethylamine derivatives represented by formula (I) and pharmaceutically acceptable acid addition salts thereof, said formula (I) being

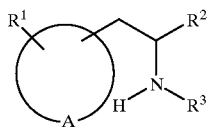

(I)

wherein $R^1$ is hydrogen, hydroxyl, lower alkoxy or halogen,
$R^2$ is alkyl having 2 to 5 carbon atoms,
$R^3$ is hydrogen, alkyl having 2 to 5 carbon atoms, alkylcarbonyl having 2 to 5 carbon atoms, aryl having 6 to 10 carbon atoms or arylalkyl having 7 to 11 carbon atoms, the ring is a bicyclic compound which comprises at least one benzene ring and may comprise a saturated or unsaturated five- or six-membered ring which may or may not have heteratoms, with the proviso that when the ring is indole or 1,3-benzodioxole, $R^2$ and $R^3$ do not constitute, at the same time, two carbon atom alkyl, and when $R^3$ is hydrogen, $R^2$ is alkyl having 3 to 5 carbon atoms and the ring is a bicyclic compound which is not indole, benzothiophene or benzodioxole.

2. The ethylamine derivatives and pharmaceutically acceptable acid addition salts thereof according to claim 1, wherein $R^3$ is alkyl having 2 to 5 carbon atoms, aryl having 6–10 carbon atoms or arylalkyl having 7 to 11 carbon atoms.

3. The ethylamine derivatives and pharmaceutically acceptable acid addition salts thereof according to claim 1, wherein $R^1$ is hydrogen and/or $R^2$ and $R^3$ are propyl.

4. The ethylamine derivatives and pharmaceutically acceptable acid addition salts thereof according to claim 1, wherein the ring is naphthalene, indole, benzofuran or 1,3-benzodioxole.

5. The ethylamine derivatives and pharmaceutically acceptable acid addition salts thereof according to claim 1, wherein the compound of formula (I) is any one of the following: 1-(2-naphthyl)-2-propylaminopentane, 1-(6-methoxy-2-naphthyl)-2-propylaminopentane, 1-(indol-3-yl)-2-propylaminopentane, 1-(indol-4-yl)-2-propylaminopentane, 1-(indol-6-yl)-2-propylaminopentane, 1-(benzofuran-2-yl)-2-propylaminopentane, 1-(Benzodioxol-4-yl)-2-propylaminopentane or 1-(Benzodioxol-5-yl)-2-propylaminopentane.

6. A composition comprising the ethylamine derivatives and/or pharmaceutically acceptable acid addition salts thereof according to claim 1 and a pharmaceutically acceptable carrier.

7. A pharmaceutical composition comprising a therapeutically effective amount of the ethylamine derivatives and/or pharmaceutically acceptable acid addition salts thereof according to claim 1 and a pharmaceutically acceptable carrier.

8. A method for treating mental disorders comprising administering a therapeutically effective amount of the ethylamine derivatives and/or pharmaceutically acceptable acid addition salts thereof according to claim 1.

9. A method for treating depression comprising administering a therapeutically effective amount of the ethylamine derivatives and/or pharmaceutically acceptable acid addition salts thereof according to claim 1.

10. A method for treating Parkinson's disease comprising administering a therapeutically effective amount of the ethylamine derivatives and/or pharmaceutically acceptable acid addition salts thereof according to claim 1.

11. A method for treating Alzheimer's comprising administering a therapeutically effective amount of the ethylamine derivatives and/or pharmaceutically acceptable acid addition salts thereof according to claim 1.

\* \* \* \* \*